(12) United States Patent
Wang

(10) Patent No.: US 12,364,854 B2
(45) Date of Patent: *Jul. 22, 2025

(54) INTRAVASCULAR BLOOD PUMP HAVING MULTILAYER CORELESS COILS

(71) Applicant: ABIOMED, Inc., Danvers, MA (US)

(72) Inventor: Jimpo Wang, Danvers, MA (US)

(73) Assignee: ABIOMED, Inc., Danvers, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/659,076

(22) Filed: May 9, 2024

(65) Prior Publication Data

US 2024/0399136 A1    Dec. 5, 2024

Related U.S. Application Data

(63) Continuation of application No. 18/131,430, filed on Apr. 6, 2023, now Pat. No. 12,011,583, which is a
(Continued)

(51) Int. Cl.
*H02K 3/28* (2006.01)
*A61M 60/17* (2021.01)
(Continued)

(52) U.S. Cl.
CPC .......... *A61M 60/419* (2021.01); *A61M 60/17* (2021.01); *A61M 60/237* (2021.01);
(Continued)

(58) Field of Classification Search
CPC .. A61M 60/419; A61M 60/17; A61M 60/237; A61M 60/416; A61M 60/508;
(Continued)

(56) References Cited

U.S. PATENT DOCUMENTS 5,850,318 A    12/1998  Dunfield et al.
5,928,131 A    7/1999   Prem
(Continued)

FOREIGN PATENT DOCUMENTS

CN    101573859 A    11/2009
CN    103893849 A    7/2014
(Continued)

OTHER PUBLICATIONS

International Search Report and Written Opinion for International Application No. PCT/US2020/039118 dated Oct. 21, 2020.
(Continued)

*Primary Examiner* — Thomas Truong
(74) *Attorney, Agent, or Firm* — Botos Churchill IP Law LLP

(57) ABSTRACT

There is provided an intravascular blood pump for insertion into a patient's heart. The blood pump comprises a slotless permanent magnet motor contained within a housing, the motor having p magnet pole pairs and n phases, where p is an integer greater than zero, and n is an integer ≥3. The motor comprises a stator extending along a longitudinal axis of the housing and having 2np coils wound to form two coils per phase per magnet pole pair. The stator comprises inner and outer windings each comprising np coils electrically connected such that the current flowing through the coils is in the same direction, the coils of the outer winding arranged on an outer surface of the coils of the inner winding.

20 Claims, 10 Drawing Sheets

Related U.S. Application Data continuation of application No. 16/909,028, filed on Jun. 23, 2020, now Pat. No. 11,648,389.

(60) Provisional application No. 62/868,530, filed on Jun. 28, 2019.

(51) Int. Cl.

| | | |
|---|---|---|
| *A61M 60/237* | (2021.01) | |
| *A61M 60/416* | (2021.01) | |
| *A61M 60/419* | (2021.01) | |
| *A61M 60/508* | (2021.01) | |
| *H02K 1/27* | (2022.01) | |
| *H02K 1/278* | (2022.01) | |
| *H02K 15/03* | (2006.01) | |

(52) U.S. Cl.
CPC ........ *A61M 60/416* (2021.01); *A61M 60/508* (2021.01); *H02K 1/278* (2013.01); *H02K 3/28* (2013.01); *A61M 2205/3334* (2013.01); *H02K 15/03* (2013.01)

(58) Field of Classification Search
CPC . A61M 2205/3334; H02K 1/278; H02K 3/28; H02K 15/03
See application file for complete search history.

(56) References Cited

U.S. PATENT DOCUMENTS

| | | | |
|---|---|---|---|
| 6,368,083 | B1 | 4/2002 | Wampler |
| 7,011,620 | B1 | 3/2006 | Siess |
| 7,462,019 | B1 | 12/2008 | Allarie et al. |
| 8,002,518 | B2 | 8/2011 | Woodard et al. |
| 10,177,627 | B2 | 1/2019 | Noh et al. |
| 11,648,389 | B2 * | 5/2023 | Wang ..................... H02K 21/14 600/16 |
| 12,011,583 | B2 * | 6/2024 | Wang ....................... H02K 3/47 |
| 2004/0017125 | A1 | 1/2004 | Nakamura et al. |
| 2007/0156006 | A1 * | 7/2007 | Smith .................. A61M 60/216 600/16 |
| 2010/0090558 | A1 | 4/2010 | Suzuki et al. |
| 2010/0253167 | A1 | 10/2010 | Sheppard et al. |
| 2012/0098371 | A1 | 4/2012 | Pinneo et al. |
| 2012/0306310 | A1 | 12/2012 | Takeuchi et al. |
| 2013/0119813 | A1 | 5/2013 | Suzuki et al. |
| 2018/0254679 | A1 | 9/2018 | Bernhardt et al. |
| 2019/0238020 | A1 | 8/2019 | Frank et al. |

FOREIGN PATENT DOCUMENTS

| | | |
|---|---|---|
| CN | 107104570 A | 8/2017 |
| CN | 108883216 A | 11/2018 |
| CN | 111082575 A | 4/2020 |
| JP | H11341725 A | 12/1999 |
| JP | 2003515392 A | 5/2003 |
| JP | 2005287285 A | 10/2005 |
| JP | 2010515418 A | 5/2010 |
| JP | 2012253922 A | 12/2012 |
| KR | 20090105939 A | 10/2009 |
| WO | 2008085466 A1 | 7/2008 |
| WO | 2018139245 A1 | 8/2018 |

OTHER PUBLICATIONS

Office Action from corresponding Chinese Patent Application No. 2020800568668 dated Apr. 6, 2024 (16 pp.).

Office Action issued in Japanese Patent Application No. 2021-577252 on Mar. 4, 2024 (9 pp.).

Office Action from corresponding Chinese Patent Application No. 2020800568668 dated Dec. 31, 2024 (13 pp.).

Search Report from corresponding Taiwanese Patent Application No. 113132659 dated Dec. 3, 2024 (5 pp.).

Office Action from corresponding Korean Patent Application No. 10-2022-7003126 dated May 28, 2025 (16 pp.).

* cited by examiner

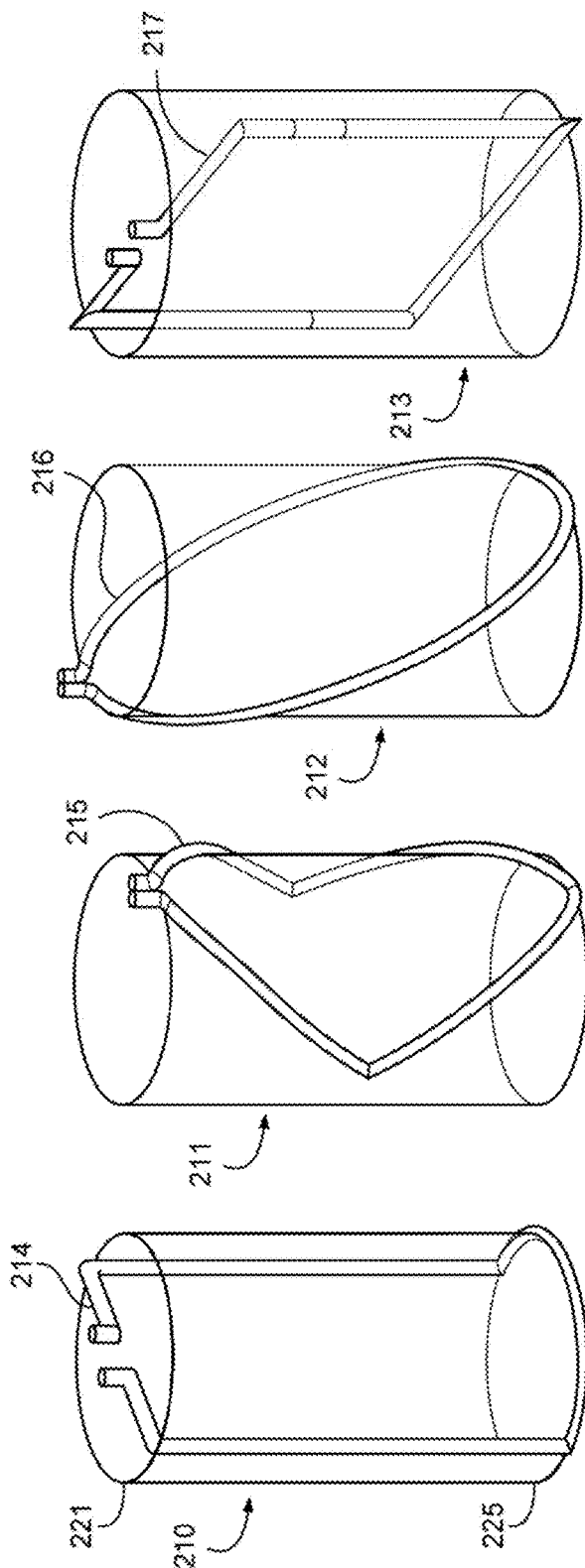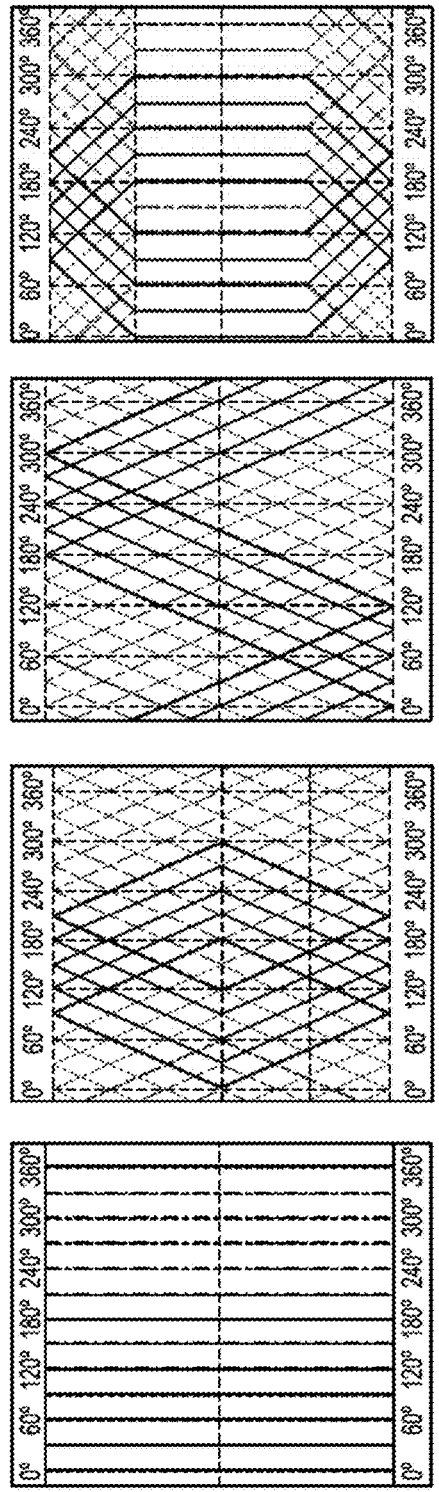

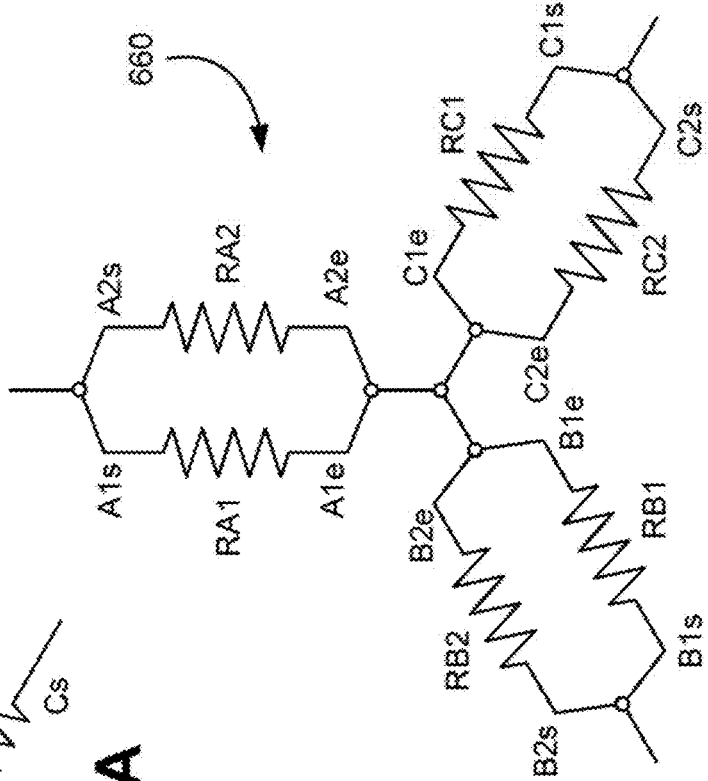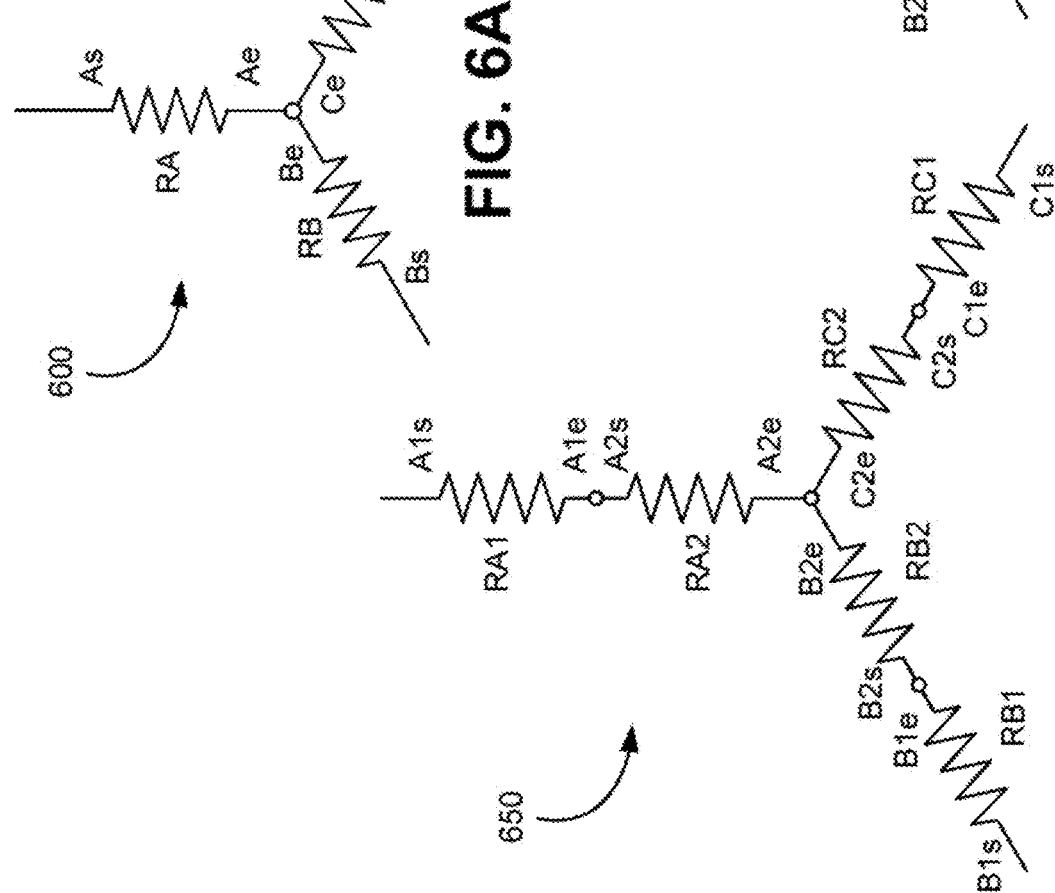
FIG. 6A
FIG. 6B
FIG. 6C

INTRAVASCULAR BLOOD PUMP HAVING MULTILAYER CORELESS COILS

CROSS-REFERENCE TO RELATED APPLICATIONS

This application is a continuation of U.S. application Ser. No. 18/131,430, filed Apr. 6, 2023, now U.S. Pat. No. 12,011,583, which is a continuation of U.S. application Ser. No. 16/909,028, filed Jun. 23, 2020, now U.S. Pat. No. 11,648,389, which claims the benefit of the U.S. Provisional Application No. 62/868,530, filed Jun. 28, 2019, all of which are incorporated herein by reference.

TECHNICAL FIELD

The present technology relates to intravascular blood pumps systems with a permanent magnet motor and a stator having coils.

BACKGROUND

Intravascular blood pumps such as the Impella® pump by Abiomed, Inc. of Danvers, MA, are quickly becoming the current standard for ventricular assist devices. The range of Impella® pumps currently comprise the Impella 2.5® pump, the Impella 5.0® pump, the Impella CPR pump and the Impella LD® pump. These pumps are inserted into a patient percutaneously through a single access point (e.g. radial access, femoral access, axillary access) such that the pump head can be placed into the left ventricle of the patient's heart via small diameter (6-7Fr) catheters. The pump head comprises an electric motor that includes a stator configured to magnetically interact with a rotor for rotation thereof thereby resulting in a volumetric flow of blood through the rotor and hence through the heart of the patient.

Currently the Impella® pump is capable of delivering blood at flow rates between about 1.0 to about 6.0 liters per minute (lpm). However, with the increased use of Impella® in a growing number of surgical procedures, a greater demand is being placed on the need to increase the blood flow rates produced beyond these levels. This essentially means a higher rotor speed is required from the electric motor. However due to the small geometries involved, increasing the rotor speed has several implications that may affect the operation of such small sized pumps. For example, increasing the rotor speed may involve the increase in generation of heat (joule heating) within the electric motor. As the device is percutaneously inserted into the heart, any such increase in heat generation may have disastrous effects. Another consideration is the resistive load placed on the device where any modifications to the electrical motor to achieve a higher flow rate may lead to a higher resistive loss.

Various techniques have been used to increase the torque constant and/or efficiency of a motor which includes increasing the number of winding turns and the packing density of coils within the motor. However, such topologies are limited by the constraints placed on motors such as the size of the motor (e.g. diameter and/or length). This has led to the implementation of post processing methods, for example mechanical squeezing of coils, to adhere to the constraints of the motor dimensions, however such methods have compromised the reliability of the motor, for example damaged insulation of the wires forming the coil, leading to short circuits.

Given the shortcomings in the state of the art as identified above, there is significant need for increasing the flow rate produced by electric motors while maintaining or increasing the efficiency of the motor.

BRIEF SUMMARY

Disclosed herein are devices for addressing various problems and shortcomings of the state of the art, as identified above. More particularly, disclosed herein are intravascular blood pumps for insertion into the patient's heart. The blood pump comprises an elongate housing having a proximal end connected to a catheter and a distal end coupled to the pump, the housing having a longitudinal axis. The blood pump also comprises a slotless permanent magnet motor contained within the housing, the motor having p magnet pole pairs and n phases, where p is an integer greater than zero, and n is an integer $\geq 3$. The motor comprises a stator extending along the longitudinal axis of the housing and having 2np coils wound to form two coils per phase per permanent magnet pole pair. The stator comprises an inner winding comprising np coils in which one coil from each phase is arranged next to a coil from a different phase in a sequential order of phase per pole pair, the arrangement repeated about the circumference of the stator for all pole pairs such that each coil of the inner winding spans $360/(np)$ mechanical degrees about the cross section of the stator, the inner winding having an exterior surface. The stator also comprises an outer winding also comprising np coils arranged on the exterior surface of the inner winding, the coils from each phase in the outer winding circumferentially aligned with the coils from the inner winding having the same phase per pole pair such that each coil of the outer winding also spans $360/(np)$ mechanical degrees about the cross section of the stator. In the stator, the coils of the same phase per pole pair are connected such that the current flowing through the coils is in the same direction. The coil windings described herein are formed from magnet wire. Magnet wires are well known to one skilled in the art and are not described in detail herein. Additionally, the motor comprises a magnet supported for rotation upon magnetic interaction with the stator thereby facilitating the flow of blood through the pump.

In another embodiment, there is provided a slotless permanent magnet electric motor having p magnet pole pairs and n phases, where p is an integer greater than zero, and n is an integer $\geq 3$, the motor having a longitudinal axis. The motor comprises a stator extending along the longitudinal axis of the housing and having 2np coils wound to form two coils per phase per permanent magnet pole pair. The stator comprises an inner winding comprising np coils in which one coil from each phase is arranged next to a coil from a different phase in a sequential order of phase per pole pair, the arrangement repeated about the circumference of the stator for all pole pairs such that each coil of the inner winding spans $360/(np)$ mechanical degrees about the cross section of the stator, the inner winding having an exterior surface. The stator also comprises an outer winding also comprising np coils arranged on the exterior surface of the inner winding, the coils from each phase in the outer winding circumferentially aligned with the coils from the inner winding having the same phase per pole pair such that each coil of the outer winding also spans $360/(np)$ mechanical degrees about the cross section of the stator. In the stator, the coils of the same phase per pole pair are connected such that the current flowing through the coils is in the same direction. Additionally, the motor comprises a magnet supported for rotation upon magnetic interaction with the stator thereby facilitating rotation of the rotor.

In some implementations, the outer winding comprises at least the same number of winding turns as the inner winding. In certain implementations, each coil comprises two layers of magnet wires, each extending longitudinally along the length of the stator. In some implementations, the magnet wires in each coil are arranged next to each other in a sequential order along the span of the coil. In further implementations, the inner winding of coils establishes a uniform foundation upon which the outer winding of coils is overlaid. In other implementations, the coils of a phase are connected to the coils of the other phases in either a star or a delta configuration. In some implementations, the coils of each phase are connected either in series or in parallel.

In certain implementations, the 2np coils comprise any one of helical windings, rhombic windings, conventional windings and hybrid windings. In further implementations, the motor comprises a three-phase one pole pair machine. In other implementations, the motor comprises a six-coil two-pole machine, each coil spanning 120 mechanical degrees about the cross section of the stator. In some implementations, the rotor pumps blood at a rate between about 1.0 lpm and about 6.0 lpm. In other implementations, the pump may be inserted into the right ventricle of the patient's heart. In further implementation, the pump may be inserted into the left ventricle of the patient's heart.

The arrangement of 2np coils wound to form two coils per phase per magnet pole pair in a double winding comprising np coils in an inner winding and np coils in an outer winding enables more wires to be used within the space available within an electric motor, thereby providing for better utilization of the motor space design. This improves the efficiency of the motor compared to motors using single-winding stators.

In a further embodiment, there is provided a method of forming a stator for use in a slotless permanent magnet motor, the motor having p magnet pole pairs and n phases, where p is an integer greater than zero, and n is an integer ≥3, the stator extending longitudinally and comprising 2np coils wound to form two coils per phase per permanent magnet pole pair. The method comprises forming an inner winding comprising np coils in which one coil from each phase is arranged next to a coil from a different phase in a sequential order of phase per pole pair, the arrangement repeated about the circumference of the stator for all pole pairs such that each coil of the inner winding spans 360/(np) mechanical degrees about the cross section of the stator, the inner winding having an exterior surface. The method then comprises forming an outer winding also comprising np coils arranged on the exterior surface of the inner winding, the coils from each phase in the outer winding circumferentially aligned with the coils from the inner winding having the same phase per pole pair such that each coil of the outer winding also spans 360/(np) mechanical degrees about the cross section of the stator. Next, the method comprises connecting the coils of the same phase per pole pair electrically such that current flows through the coils in the same direction.

In some implementations, the method further comprises forming the outer winding such that the outer winding comprises at least the same number of winding turns as the inner winding. In certain implementations, the method also comprises forming the coils such that each coil comprises two layers of magnet wires, each extending longitudinally along the length of the stator. In other implementations, the magnet wires in each coil are arranged next to each other in a sequential order along the span of the respective coil. This provides for a precisely ordered and compact arrangement of magnet wires in the coils of the stator leading to a minimum coil thickness which does not require mechanical squeezing to fit into the yoke of an electric motor. The stator is the combination of the coils and the yoke. The stator thickness is the combined thickness of the coil thickness and the yoke thickness. The coil thickness described herein excludes the yoke thickness. The precisely ordered and compact arrangement of the coils enhances the reliability of the double-winding stator as there is no risk to the integrity of the insulation around the wires forming the winding. This minimum coil thickness also enables the use of a larger rotor magnet and/or a thicker magnetic steel yoke in the electric motor thereby enabling the motor to achieve a higher efficiency compared to motors employing stators in which the multiple-layer magnet wires are randomly wound.

In some implementations, the method comprises connecting the coils of a phase with the coils of other phases in either a star or a delta configuration. In certain implementations, the method comprises connecting the coils of each phase either in series or in parallel. In other implementations, the method comprises forming the 2np coils using a coil winding pattern selected from any one of: helical, rhombic, conventional and hybrid. In some implementations, the stator is suitable for use in a motor having three phases and one pole pair. In certain implementations, the stator is suitable for use in a six-coil one pole pair motor, each coil spanning 120 mechanical degrees about the cross section of the stator.

BRIEF DESCRIPTION OF DRAWINGS

The foregoing and other objects and advantages will be apparent upon consideration of the following detailed description, taken in conjunction with the accompanying drawings, in which like reference characters refer to like parts throughout, and in which:

FIGS. 2A-2D show illustrative winding patterns for individual turns in a coil, as are known in the art that may be employed in the blood pump of FIG. 1;

FIGS. 2E-2H show illustrative complete coil winding patterns formed by coils having the individual turns shown in FIGS. 2A-2D;

FIG. 6A shows an illustrative circuit diagram illustrating the lead wire connections in the single-winding stator of FIG. 3;

FIG. 6B shows an illustrative circuit diagram illustrating the lead wire connections in the double-winding stator of FIG. 4 in which coils of the same phase are connected in series, according to an embodiment of the present disclosure;

FIG. 6C shows an illustrative circuit diagram illustrating the lead wire connections in the double-winding stator of FIG. 4 where coils of the same phase are connected in parallel, according to an embodiment of the present disclosure;

DETAILED DESCRIPTION

Figure 1:
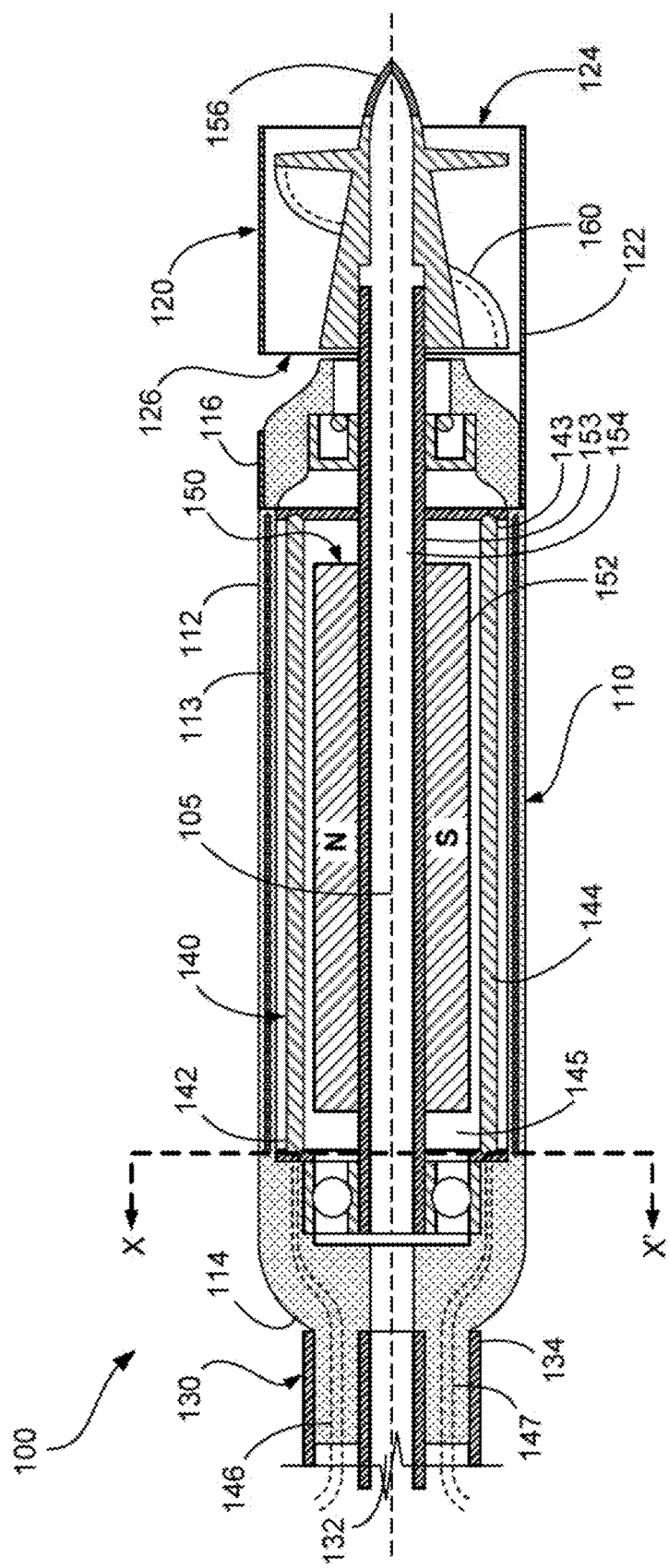
FIG. 1 shows an illustrative cross section of an intravascular blood pump, according to an embodiment of the present disclosure.

Embodiments of the present disclosure are described in detail with reference to the drawing figures wherein like reference numerals identify similar or identical elements. It is to be understood that the disclosed embodiments are merely examples of the disclosure, which may be embodied in various forms. Well-known functions or constructions are not described in detail to avoid obscuring the present disclosure in unnecessary detail. Therefore, specific structural and functional details disclosed herein are not to be interpreted as limiting, but merely as a basis for the claims and as a representative basis for teaching one skilled in the art to variously employ the present disclosure in virtually any appropriately detailed structure.

To provide an overall understanding of the devices described herein, certain illustrative embodiments will be described. Although the embodiments and features described herein are specifically described for use in connection with intravascular blood pumps, it will be understood that all the components and other features outlined below may be combined with one another in any suitable manner and may be adapted and applied to other types of procedures requiring efficient electric motors.

The devices and methods described herein relate to an intravascular blood pump for insertion into a patient's heart. The blood pump comprises an elongate housing having a proximal end connected to a catheter and a distal end coupled to the pump, the housing having a longitudinal axis. The blood pump also comprises a slotless permanent magnet motor contained within the housing, the motor having p magnet pole pairs and n phases, where p is an integer greater than zero, and n is an integer $\geq 3$. The motor comprises a stator extending along the longitudinal axis of the housing and having 2np coils wound to form two coils per phase per permanent magnet pole pair. The stator comprises an inner winding comprising np coils in which one coil from each phase is arranged next to a coil from a different phase in a sequential order of phase per pole pair, the arrangement repeated about the circumference of the stator for all pole pairs such that each coil of the inner winding spans 360/(np) mechanical degrees about the cross section of the stator, the inner winding having an exterior surface. The stator also comprises an outer winding also comprising np coils arranged on the exterior surface of the inner winding, the coils from each phase in the outer winding circumferentially aligned with the coils from the inner winding having the same phase per pole pair such that each coil of the outer winding also spans 360/(np) mechanical degrees about the cross section of the stator. In the stator, the coils of the same phase per pole pair may be connected in series or in parallel such that the current flowing through the coils is in the same direction. Additionally, the motor comprises a magnet supported for rotation upon magnetic interaction with the stator thereby facilitating the flow of blood through the pump.

The intravascular blood pump of the present disclosure employs an electric motor with a unique stator. Such a stator comprises a double-winding (or four-layer) coil which leads to an improved utilization of motor design space. This facilitates a gain in copper wire usage by the motor compared to a stator comprising a single-winding (or two-layer) coil, which accordingly considerably increases torque capability of the motor. The stator also enables the motor to achieve a higher motor constant and higher motor efficiency. It should be noted that due to the fixed geometry of the motor, when the double-winding stator is implemented instead of the single-winding stator, a smaller magnet and/or thinner yoke needs to be used due to the thicker stator coils. Thus, increasing the number of magnet wires in the double-winding stator comes with the compromise of a smaller magnet used for the rotor and/or a decrease in yoke thickness. This leads to a lower magnetic flux density. However, the effect of more magnet wires more than makes up for the reduced magnetic flux density from the smaller rotor magnet and thinner magnetic yoke. In some implementations, in order to maintain a comparable coil resistance as the single-winding stator, thicker magnet wires may be used in the double-winding stator. Such a double-winding stator comprises two coils per phase per magnet pole pair connected in the abovementioned configuration. This provides for an increase in motor torque constant by about 20% to about 50% over blood pumps employing a single-winding stator with one coil per phase per magnet pole pair. In certain implementations the motor torque constant may be increased by about 25%, about 30%, about 35%, about 40% or about 45%.

Further, conventional attempts to increase the number of magnet wires in the stator of an electric motor have resulted in non-uniform multiple-layer stators. The irregular arrangement of wires in such stators leads to a randomly wound stator which is oversized, particularly in thickness. Such randomly wound stators often require mechanical squeezing to reduce the thickness of coils by reducing the diameter of coils and/or increasing the inner diameter of coils before they can be used in electric motors. In contrast, the double-winding stator according to embodiments of the present disclosure provides for a sequential arrangement of magnet wires in each coil of the stator, thereby resulting in a stator having coils that are more compact. Due to the relatively thin coil compared with randomly wound multiple-layer stators, the double-winding stators require no or minimum mechanical squeezing prior to use which preserves the integrity of wire insulation to enhance the reliability of motors.

The following includes the description of a stator using the following terms. The stator comprises at least one winding, such as, for example, an inner winding and an outer winding, electrically connected together. Each of the windings spans 360° about the cross section of the stator. Additionally, each of the windings comprises a plurality of coils, such as, for example coils A, B and C for a three-phase electric motor, equally arranged circumferentially around the entire 360° span of the stator. For example, coils A, B and C may each span 120° about the cross section of the stator. Each coil comprises a plurality of turns N. For example, each coil may comprise 65 winding turns. Each turn of the N turns comprises a magnet wire with a forward portion that extends longitudinally from a proximal end to a distal end of the winding, and a return portion that extends from the distal end to the proximal end. When each winding (inner or outer winding) consisting of coils A, B, and C, is completed, it forms a two-layer coil. Therefore, in total, the double-winding stator forms a four-layer coil.

FIG. 1 illustrates an exemplary intravascular blood pump 100 for insertion into the heart of a patient, according to an embodiment of the present disclosure. Blood pump 100 comprises a motor unit 110 and a pump unit 120 arranged along a longitudinal axis 105. The motor unit 110 comprises an electric motor including a stator 140 and a rotor 150 contained within a housing 112. The stator 140 extends along the length of the motor unit 110 from a proximal end 142 to a distal end 143, and comprises wires 144 wound in a particular pattern, the details of which will be provided below. The stator 140 defines a central lumen 145 in which the rotor 150 is positioned. The stator 140 is slotless such that the wires 144 are wound upon themselves and not onto a laminated stator core. Feed lines 146, 147 provide the necessary electrical connections externally from the pump 100 to the stator 140 for operation of the motor unit 110. Each of the wires 144 may have an insulating coating (not shown), and, optionally, the stator 140 may be enmolded by a synthetic epoxide resin (also not shown).

In FIG. 1, the stator 140 and the housing 112 are depicted as separate components, however it will be understood that the stator 140 may be encapsulated within the housing 112 to form a single component. The housing 112 comprises a proximal end 114 and a distal end 116. The proximal end 114 of the housing 112 is coupled to a distal end 134 of a catheter 130 which may comprise a flexible tube. Catheter 130 comprises a lumen 132 which extends towards the physician (i.e. proximally) for control and operation of the blood pump 100.

The rotor 150 comprises a permanent magnet 152 that is rotationally supported about a shaft 153 within the lumen 145 of the stator 140. Magnet 152 may comprise cylindrical permanent magnet 152 that surrounds the shaft 153 within the motor unit 110. Shaft 153 extends from the motor unit 110 into the pump unit 120 and facilitates rotation of an impeller 160 for the pumping of blood. In certain implementations, the rotor 150 may comprise several permanent magnets attached to the shaft 153, or an electromagnetic magnet having its own rotor windings. Further, while FIG. 1 illustrates the rotor 150 as rotatable within the stator 140, the electric motor 110 may be configured such that the stator 140 is held stationary about the shaft 153 and the rotor 150 is configured as a cylinder that rotates around the stator 140. Shaft 153 extends along the length of the motor unit 110 and extends into a cylindrical housing 122 of the pump unit 120. In some implementations, the shaft 153 may be hollow and comprise a lumen 154 for the passage of a guidewire, for example.

The distal end of the shaft 153 is coupled to an impeller 160 located within the pump housing 122. Interaction between the stator 140 and rotor 150 of the motor unit 110 generates torque in the rotor 150 causing the shaft 153 to rotate, which, in turn, causes the impeller 160 to rotate in the cylindrical pump housing 122. When this occurs, blood is sucked into the pump via an axial intake opening 124 for conveyance in the axial direction, the blood issuing laterally from the openings 126 and flowing axially along housing 112. In this manner the pump 100 generates a flow of blood within the heart of the patient.

The electric motor also comprises a yoke 113 that is contained within the housing 112. The yoke 113 carries the magnetic flux produced by the permanent magnet poles of the rotor 150. In some cases, the housing 112 may serve as the yoke 113. As the yoke 113 is the outermost component of the electric motor, its inner diameter limits the size of the stator 140.

FIGS. 2A-2D illustrate exemplary winding patterns 210-213 according to an embodiment of the present disclosure. In FIGS. 2A-2D the individual winding turn structures of different winding patterns are shown, such as wires 142 in FIG. 1, however it will be understood that the complete stator, such as stator 140 in FIG. 1, will be obtained by the axial and angular arrangement of a plurality of wire turns about a longitudinal axis of the motor unit, such as the longitudinal axis 105 in FIG. 1. FIGS. 2E-2H illustrate the coil winding patterns for a complete stator for each of the coil winding types in FIGS. 2A-2D, respectively. The horizontal axis of each of the plots in FIGS. 2E-2H represents the angular position along the circumference of the respective stator and the vertical axis represents the longitudinal length of the respective stator moving from the distal end to the proximal end of the stator.

FIGS. 2A-2D illustrate exemplary winding patterns for individual turns in coil employed in electric machines. The winding patterns in FIGS. 2A-2D may be used in the formation of the stator 140 of the motor unit 110 in FIG. 1. FIG. 2A shows an individual coil winding pattern 210 in which each wire 214 in the coil extends from a proximal end 221, along the length of the coil, to a distal end 225. At the distal end 225, the wire 214 follows the external perimeter of the stator for 180 mechanical degrees and returns to the proximal end 221. Because the end points of the wire 214 both end up at the proximal end 221, coil winding patterns 210 may be faced with an end turn stack up issue in which each of the plurality of lead wires at the proximal end 221 of the coil winding 210 has to be electrically connected to the stator feed line(s), which, in turn, may cause crowding and connections issues. A complete coil winding pattern formed by coils having the turns illustrated in FIG. 2A is shown in FIG. 2E. FIG. 2B shows an individual rhombic coil winding pattern 211 in which each wire 215 is arranged in a bent configuration. Unlike the coil winding pattern 210 in FIG. 2A, the rhombic coil winding pattern comprises one continuous wire that is wound several times over, each complete turn shifted angularly to form the complete coil winding pattern as shown in FIG. 2F. The bent configuration of the rhombic coil winding pattern when adopted in a stator may require post-assembly of the coils of each individual phase.

FIG. 2C shows an individual helical coil winding pattern 212 in which each wire 216 is arranged in an elliptical configuration. The helical coil winding pattern 212 is similar to the rhombic coil winding pattern 211 in FIG. 2B but without the bend which simplifies the coil winding process. The helical coil winding is a one-step winding which can be easily formed without the need for any post-assembly steps. A complete coil winding pattern having the helical coil winding pattern illustrated in FIG. 2C is shown in FIG. 2G. FIG. 2D shows an individual hybrid coil winding pattern 213 that comprises a coil winding that is a mixture of the coil winding as shown in FIG. 2A and the rhombic coil winding as shown in FIG. 2B. Such a hybrid coil winding allows for the optimum ratio of torque to resistance by adjusting the horizontal to vertical aspect ratio of the coil. A complete coil winding comprising the hybrid coil winding patterns illustrated in FIG. 2D is shown in FIG. 2H.

The following disclosure makes use of the individual helical coil winding pattern of FIG. 2C, and associated complete coil winding pattern of FIG. 2G, in the respective stators. However, it will be understood that the stators in the present disclosure can employ any of winding patterns as described in relation to FIGS. 2A-2D. Further, in some implementations of the present disclosure, any other winding patterns may be employed.

Figure 4:
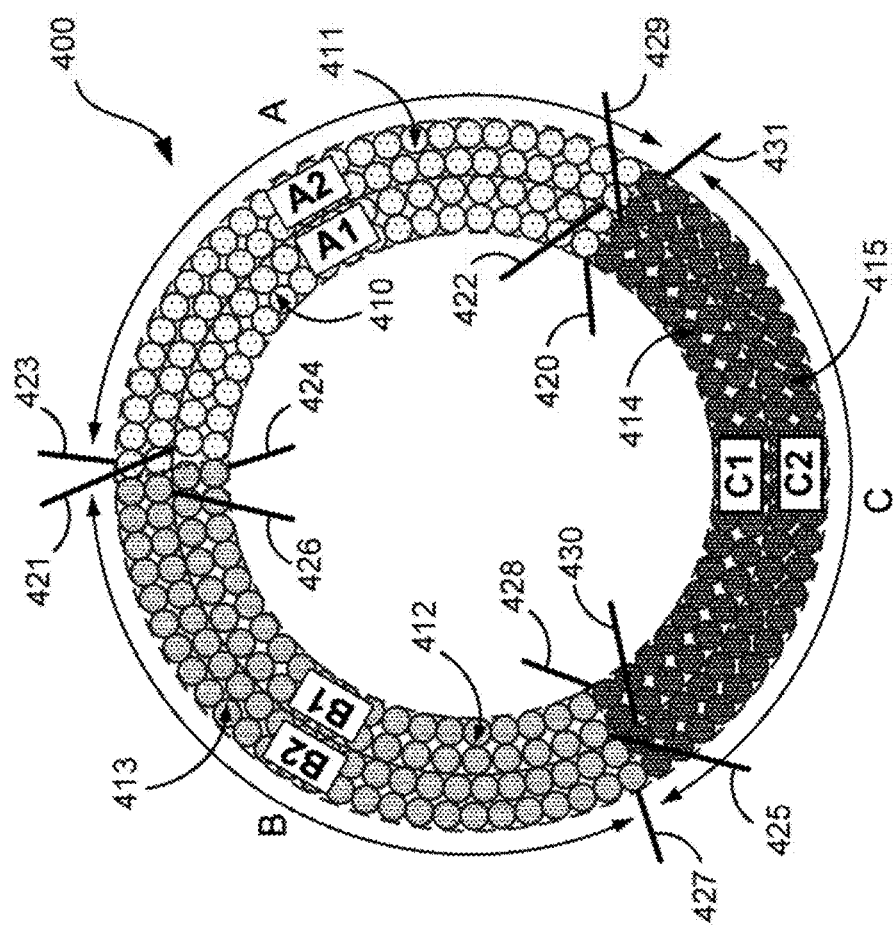
FIG. 4 shows an illustrative cross section of a three-phase double-winding stator, each phase implemented with a double helical coil, according to an embodiment of the present disclosure, for use in the blood pump of FIG. 1.
Figure 3:
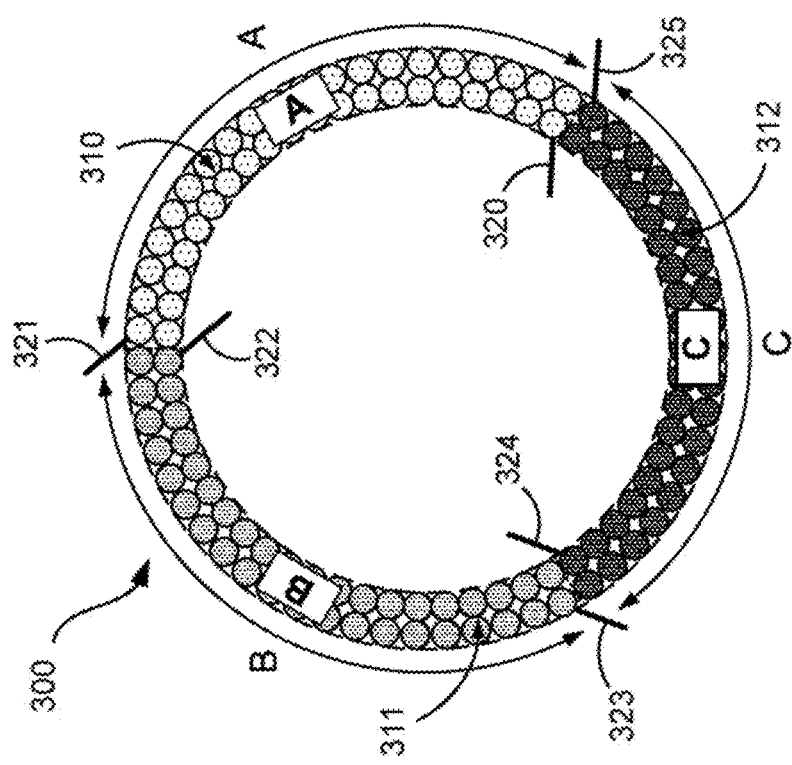
FIG. 3 shows an illustrative cross section of a three-phase-single winding stator, each phase implemented with a single helical coil, for use in the blood pump of FIG. 1.

FIGS. 3 and 4 illustrate cross sections of exemplary stators for use in an electric motor, such as stator 140 of motor unit 110 in FIG. 1. The cross sections of the stators illustrated in FIGS. 3 and 4 are taken about line X-X' as shown in FIG. 1. FIG. 3 shows a stator 300 comprising one coil per phase per magnet pole pair for use in a three-phase electric motor having once pole pair. With this arrangement, stator 300 is a single-winding stator (or a two-layer coil stator). In the present disclosure, the three phases of the electric motor are referred to as phases A, B and C. In the single-winding stator 300, each phase comprises one coil-coil 310 (labelled 'A') for phase A, coil 311 (labelled 'B') for phase B, and coil 312 (labeled 'C') for phase C. Each of the coils 310-312 comprises a winding having a plurality of N turns, where N is an integer and N>1, where each coil has the same number of turns. The windings are formed from wires that have been wound in a specific manner, such as that described in relation to FIGS. 2A-2D, thereby resulting in each coil having a start point and an end point, as indicated by the lead wires 320-325 in FIG. 3. In some implementations, the windings are formed from insulated magnet wires. Embodiments of the present disclosure will be described with respect stators having helical coils as illustrated in FIGS. 2C and 2G, however it will be understood that any winding type may be employed.

As seen in FIG. 3, the angular distribution of coils 310-312 is such that they are equally distributed about the stator 300 where each coil spans 120 mechanical degrees about the circumference of the cross section of the stator 300. While stator 300 is employed in a three-phase electric motor having one coil per magnet pole pair, for a general electric motor having n phases and p magnet pole pairs, each coil of a single-winding stator having one coil per phase per magnet pole pair would span 360/(np) mechanical degrees about the circumference of the cross section of the stator. As for the axial distribution of the coils about the longitudinal axis of the single-winding stator 300, the windings of the coils 310-312 are configured such that they are each wound from the proximal end of the stator 300 (such as proximal end 142 of stator 140 in FIG. 1), extending longitudinally towards the distal end (such as distal end 143 of stator 140 in FIG. 1), and returning back to the proximal end. In this manner, each of the coils 310-312 of the stator 300 effectively comprises a single winding. In the configuration shown in FIG. 3, the lead wires for each of the coils 310-312 are located at the proximal end of the stator 300 for connectivity with the feed lines to the electric motor, such as feed lines 146, 147 as shown in FIG. 1.

It should be noted that the lead wires 320-325 for each coil 310-312 are located on cither end of the span of the respective coils due to the manner in which the single-winding stator is formed. For example, coil A is formed by winding a wire from a first end 320 along the circumference of the stator about the 120° span of the coil in a first direction (e.g. anticlockwise) until the end of the span of the coil where the magnet wire forms a second end 321. Further, in the single-winding stator 300, coil A is formed in entirety before coils B and C are formed.

FIG. 4 shows a stator 400 comprising two coils per phase per magnet pole pair for use in a three-phase electric motor having one pole pair, according to an embodiment of the present disclosure. With this arrangement, stator 400 is a double-winding stator (or a four-layer coil stator), and, when implemented with the individual helical coil winding pattern as depicted in FIG. 2C, the stator 400 is a double helical winding stator similar to the complete winding illustrated in FIG. 2G. In the stator 400, each phase A, B and C of the three-phase electric motor comprises two coils. Thus, phase A comprises coil 410 (labelled 'A1') and coil 411 (labelled 'A2'), phase B comprises coil 412 (labelled 'B1') and coil 413 (labelled 'B2'), and phase C comprises coil 414 (labelled 'C1') and coil 415 (labelled 'C2'). Further, as shown in FIG. 4, stator 400 has an inner winding comprising coils A1, B1 and C1, and an outer winding comprising coils A2, B2 and C2.

With reference to the single-winding stator 300 in FIG. 3, the double-winding stator 400 of the present disclosure is a thicker coil which may have a smaller inner diameter and/or larger outer diameter than the single-winding stator 300. In certain implementations, thicker magnet wires are used in the double-winding stator 400 compared to the wires used for the single-winding stator 300 in order to maintain comparable coil resistance. Thus, if each coil 310-312 of the single-winding stator 300 comprises a winding having N turns, where N is an integer and N≥1, the coils for each phase A, B and C in the double-winding stator 400 comprise windings having about 1.5N turns to about 2N turns, with each coil A1, B1 and C1 in the inner winding having the same number of turns, and each coil A2, B2 and C2 in the outer winding having the same number of turns. However, due to the increase in diameter of the double-winding stator 400, it should be noted that each of coils A2, B2 and C2 in the outer winding have a greater number of turns than each of coils A1, B1 and C1 in the inner winding. It should be noted that the double-winding stator 400 is implemented with thicker magnet wires to lower the coil resistance, thereby resulting in the double-winding stator having about 1.5N turns to about 2N turns. As described in the foregoing, coils 410-415 are each formed from helical windings having a start point and an end point, as indicated by the lead wires 420-431 in FIG. 4.

The angular distribution of coils 410-415 is such that they are equally distributed about the stator 400 where each coil spans 120 mechanical degrees about the circumference of the cross section of the stator 400. While stator 400 is employed in a three-phase electric motor having two coils per phase per magnet pole pair, for a general electric motor having n phases and p magnet pole pairs, the stator 400 comprises an inner winding and an outer winding. The inner winding comprises np coils in which one coil from each phase is arranged next to a coil from a different phase in a sequential order of phase per pole pair, the arrangement repeated about the circumference of the stator for all pole pairs such that each coil of the inner winding spans 360/(np) mechanical degrees about the cross section of the stator. The inner winding provides an exterior surface on which the coils of the outer winding are formed. The outer winding also comprises np coils, arranged on the exterior surface of the inner winding, the coils from each phase in the outer winding circumferentially aligned with the coils from the inner winding having the same phase per pole pair such that each coil of the outer winding also spans 360/(np) mechanical degrees about the cross section of the stator.

The winding pattern of the individual coils A1, B1, and C1 in the double-winding stator 400 is the same as that of the individual coils A, B and C in the single-winding stator 300. However in the double-winding stator 400, after the inner winding is formed, the windings of coils 411, 413, 415 forming the outer winding are each wound on the exterior surface of coils 410, 412, 414 forming the inner winding, from the proximal end of the stator 400, extending longitudinally towards the distal end, and returning back to the proximal end. In this manner the inner winding and the outer winding effectively comprise two layers of wires each, hence termed a four-layer coil stator. The lead wires for each of the coils 410-415 are located at the proximal end of the stator 400 for connectivity with the feed lines to the electric motor, such as feed lines 146, 147 as shown in FIG. 1.

It should be noted that lead wires 420-421, 424-425 and 428-429 for coils 410, 412, 414, respectively, of the inner winding and lead wires 422-423, 426-427 and 430-431 for coils 411, 413, 415, respectively, of the outer winding are located on either end of the span of the respective coils due the manner in which the double-winding stator 400 is formed. For example, coil A1 is formed by winding the coil from a first end 420 along the circumference of the stator about the 120° span of the coil in a first direction (e.g. anticlockwise) until the end of the span of the coil where the magnet wire forms a second end 421. After forming coil A1, the coils comprising the rest of the inner winding (i.e. coils B1 and C1) are then formed. Only once the inner winding is completely formed does the formation of the coils comprising the outer winding begin. Thus, after coils A1, B1 and C1 are formed, coils A2, B2 and C2 are formed. Coil A2 is formed by winding the coil from a first end 422 along the circumference of the stator about the 120° span of the coil in a first direction (e.g. anticlockwise) until the end of the span of the coil where the magnet wire forms a second end 423. After coil A2 is formed, the coils comprising the rest of the outer winding are then formed. The winding sequence of the present disclosure leads to a winding in which the wires are precisely ordered to achieve a four-layer coil stator that is as compact as possible. This preserves the integrity of the wires forming the respective coils, as will be detailed in the following sections relating to FIGS. 9A-9B.

It should be noted that the double-winding stator 400 is at least twice as thick as the single-winding stator 300. This means the double-winding stator 400 may have a smaller inner diameter and/or larger outer diameter than the single-winding stator 300. When the double-winding stator 400 is used in an electric motor a smaller magnet and/or a thinner yoke will be needed due to the fixed dimensions within the electric motor. The smaller magnet and/or a thinner yoke both lower the magnetic flux density and thus compromise the motor torque constant and motor efficiency. However, the benefit from the increased number of coil winding turns within the double-winding stator 400 compared to the single-winding stator 300 outweigh the smaller magnet and/or a thinner yoke, thereby resulting in a considerable increase in motor torque constant and motor efficiency.

Figure 5:
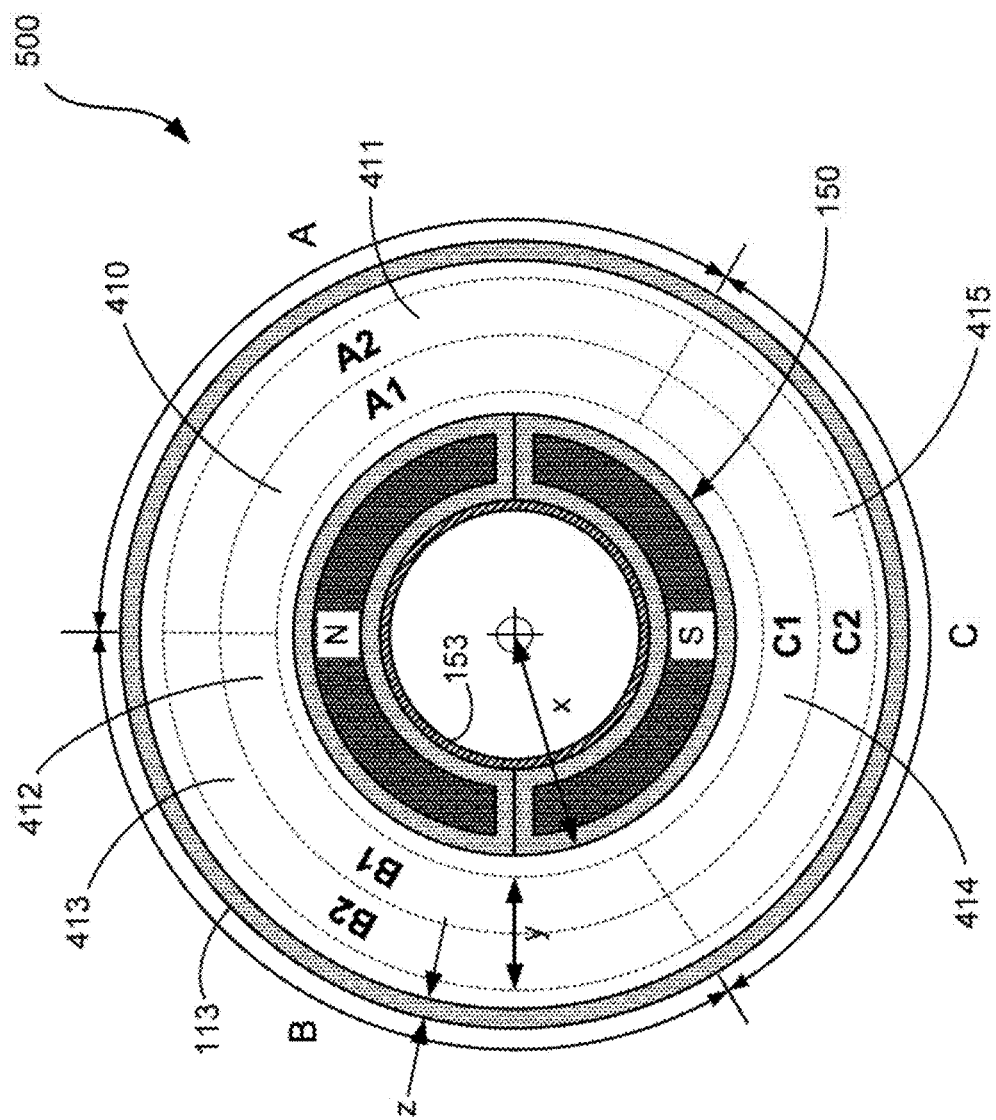
FIG. 5 shows an illustrative cross section of the stator of FIG. 4 used in the blood pump of FIG. 1, according to an embodiment of the present disclosure.

FIG. 5 illustrates an exemplary cross-section 500 of the electric motor 110 of the blood pump 100 of FIG. 1 employing the double-winding stator 400 in a three-phase two-pole electric motor. For clarity the windings forming coils 410-415 are omitted from FIG. 5. The interaction of the current flowing in the coils of the stator 400 with the magnetic flux density of the two-pole rotor during operation will be described with reference to FIG. 5. As described in relation to FIG. 1, rotor 150 is in constant rotation when in use. FIG. 5 depicts the position of the rotor 150 at an instant when the rotor is positioned as shown. In the illustrated position, the permanent magnet rotor 150 produces a magnetic flux density B, and each of the coils 410-415 carry a current that may be directed longitudinally (into the page or out of the page). According to Lorentz force law, the interaction between the magnetic flux density B and the longitudinal length of the current-carrying wire L in a direction perpendicular to the magnetic flux density B generates a torque T within the rotor 150 for rotation thereof, governed by the equation:

$$T \propto (L\hat{z} \times B\hat{r}), \tag{1}$$

where $\hat{z}$ is a direction parallel to the longitudinal axis 105 of the rotor 150, $\hat{r}$ is a radial direction of the magnetic flux density B that is perpendicular to the longitudinal axis 105 of the rotor 150, and x denotes the vector cross product. Thus, the flow of current in stator 400 causes rotation of the rotor 150 about the longitudinal axis 105, which, in turn, causes a corresponding rotation of the impeller 160 coupled to the distal end of the rotor shaft 153. With marginal reduction in magnetic flux density B, the stator 400 described herein attempts to increase L considerably in order to increase the torque production in the motor.

The double-winding stator 400 of the present disclosure increases the number of winding turns of the electric motor compared to a single-winding stator by doubling the number of coils per phase. However, as will be discussed in relation to FIGS. 9A-9B, the double-winding stator of the present disclosure is not only concerned with doubling the number of coils per phase. Rather, the double-winding stator 400 of the present disclosure is formed using a unique winding sequence in which wires forming the coils of the inner winding are first formed in a sequential order, after which wires forming the coils of the outer winding are formed on the outer surface of the inner winding in a sequential order. Such a winding sequence increases the packing density of the coils between the outer diameter of the rotor 150 and the inner diameter of the yoke 113. Thus, the double-winding stator 400 of the present disclosure considerably increases the L component of equation (1) as the number of current-carrying wires of the stator 400 increases, and does not require the reduction of the magnet size and the thickness of the magnetic yoke.

As briefly discussed in relation to FIG. 1, the outer diameter of the pump 100 is limited by the inner diameter of the catheter used to position the pump within the heart of the patient. Currently the maximum inner diameter of the catheter used for the Impella® pump is about 14 Fr. The dimension x+y+z of the electric motor, as shown in FIG. 5, where x is the radius of the rotor 150, y is the thickness of the stator coil, and z is the thickness of the yoke 113, is therefore constrained by the inner diameter of the catheter. In order to increase the magnetic flux density B in the motor, (i) larger permanent magnets can be used (i.e. larger x), (ii) the coil can be made thinner (i.e. smaller y), and (iii) a thicker yoke can be used (i.e. larger z).

With respect to the design of the double-winding stator 400, the magnetic flux density B of the motor is reduced due to thicker double-winding stator coils (larger y) and the resulting smaller permanent magnets (smaller x) and/or thinner yoke (smaller z) that are required due to the space constraints within the catheter, when compared to the single-winding stator 300. This decreases the B component in equation (1). However, the increase in L due to the larger number of winding turns of coils is greater than the decrease in B for the reasons described above. The net effect is that the torque generated in the rotor 150 increases.

Coils 310-312 in the single-winding stator 300 and coils 410-415 of the double-winding stator 400 of the present disclosure may be electrically connected in any configuration for electric motors, such as, for example, a star connection or a delta connection. FIG. 6A shows the coils 310-312 of the single-winding stator 300 in FIG. 3 connected in an exemplary star configuration 600. Coils 310-312 are represented as their resistances RA, RB and RC, respectively. In FIG. 6A (and FIGS. 6B and 6C that follow), 's' denotes the starting lead wire of a coil and 'e' denotes the ending lead wire of a coil. In the star configuration 600, the end point 'Ae' of coil 310, the end point 'Be' of coil 311, and the end point 'Ce' of coil 330, are connected together. The start point 'As' of coil 310, the start point 'Bs' of coil 311, and the start point 'Cs' of coil 312, are connected to a feed line, such as feed lines 146, 147 of the blood pump 100 in FIG. 1. In this manner, each branch of the star configuration 600 comprises a single load corresponding to the coils for each phase in the single-winding stator 300.

FIG. 6B shows an exemplary electrical connection of the coils in the double-winding stator 400, according to an embodiment of the present disclosure. FIG. 6B shows the coils of the stator 400 connected in a star configuration in which the coils for each phase A, B and C are connected in series. Here coils 410-411 are represented as resistances RA1 and RA2 for phase A, respectively, coils 412-413 are represented as resistances RB1 and RB2 for phase B, respectively, and coils 414-415 are represented as resistances RC1 and RC2 for phase C, respectively. As mentioned in the foregoing, stator 400 comprises coils arranged in an inner winding and an outer winding. The coils 410, 412, 414 of the inner winding each comprise N turns, while the coils 411, 413 and 415 of the outer winding each comprise at least N turns, where N is the number of turns of in each coil of the stator 300, the total number of winding turns per phase in the double-winding stator 400 may be 1.5 to 2.0 times of that of the single-winding stator 300. Thus, the electrical resistance per phase of the double-winding stator 400 is higher than that of the single-winding stator 300. It should be noted that in some implementations, thicker magnet wires are used in the double-winding stator 400 to achieve a comparable resistance as compared to the single winding stator 300.

It is known that the motor efficiency can be implied by the motor constant $K_m$, which, in turn, is defined as:

$$K_m \propto \frac{K_T}{\sqrt{R}}, \quad (2)$$

where $k_T$ is the torque constant and R is the coil resistance. Further, it is known that the torque constant $k_T$ is the torque T per unit current I, and thus the torque constant can be determined using the relation:

$$K_T \propto (L\hat{z} \times B\hat{r}), \quad (3)$$

where B is the magnetic flux density and L is the length of the current-carrying wire in a direction perpendicular to the magnetic flux density.

As discussed with respect to FIG. 5, the double-winding stator 400 of the present disclosure increases the contribution of L by about 1.5 to about 2 times while marginally reducing the contribution of B to the generated torque T in the rotor 150 due to the larger y (thicker coils), smaller x (smaller magnet) and/or smaller z (thinner yoke) when compared to the single-winding stator 300. According to equations (1) and (3), this increases the motor torque constant $k_T$ by about 20% to about 50%. In other implementations, the motor torque constant may be increased by about 25%, about 30%, about 35%, about 40% or about 45%. Further, as the number of turns per phase in the double-winding stator 400 is increased compared to a single-winding stator 300, a thicker wire is used to achieve comparable coil resistance as single-winding stator 300. Thus, from equation (2), it is expected that the double-winding stator 400 of the present disclosure increases the motor constant $K_m$ over that of the single-winding stator 300. This leads to an increased motor efficiency.

As shown in the connection diagram of FIG. 6B, each branch of the star configuration 650 comprises two coils connected in series such that the current flowing through the coils of the same phase is in the same direction, i.e. the two coils are connected in a manner where the end point of one coil is connected to the start point of the other coil. For example, for phase A, coils 410-411 represented by resistances RA1 and RA2, respectively, are connected such that the end point 'A1e' is connected to the start point 'A2s'. Similarly, end point 'B1e' of coil 413 and start point 'B2s' of coil 414 of phase B, represented by resistances RB1 and RB2, respectively, are connected together, and end point 'C1e' of coil 414 and start point 'C2s' of coil 415 of phase C, represented by resistances RC1 and RC2, respectively, are connected together. The start point 'A1s' of the resistance RA1 of coil 410 for phase A, the start point 'B1s' of the resistance RB1 of coil 412 for phase B, and the start point 'C1s' of resistance RC1 of coil 414 for phase C, are connected to a feed line, such as feed lines 146, 147 of the blood pump 100 in FIG. 1. Additionally, the end point 'A2e' of the resistance RA2 of coil 411 for phase A, the end point 'B2e' of the resistance RB2 of coil 413 for phase B, and the end point 'C2e' of resistance RC2 of coil 415 for phase C, are connected together.

The manner in which the coils 410-415 of the double-winding stator 400 of the present disclosure are connected is important as it determines how the coils 410-415 interact with the magnetic flux density generated by the rotor 150 during operation of the electric motor. With the star configuration 650 as depicted in FIG. 6B, the direction of current flowing through coil A1 of stator 400 is the same as the direction of current flowing through coil A2. Similarly, the direction of current flowing through coil B1 of stator 400 is the same as the direction of current flowing through coil B2, and the direction of current flowing through coil C1 of stator 400 is the same as the direction of current flowing through coil C2. This means that coils A1 and A2, having the same direction of current flowing therethrough, both interact with the same pole of the rotor. Additionally, coils B1 and B2, having the same direction of current flowing therethrough, both interact with the same pole of the rotor. Further, coils C1 and C2, having the same direction of current flowing therethrough, both interact with the same pole of the rotor. In effect, the coils of each phase in the double-winding stator 400 of the present disclosure see the same polarity of the magnet per pole pair of the rotor.

FIG. 6C shows a further exemplary electrical connection of the coils in the double-winding stator 400, according to an embodiment of the present disclosure. In FIG. 6C the coils of the stator 400 are connected in a star configuration 660 in which the coils for each phase A, B and C are connected in parallel such that the current flowing through the coils is in the same direction. This can be seen in FIG. 6C where, for phase A, coils 410-411 represented by resistances RA1 and RA2, respectively, are connected such that the end points 'A1e' and 'A2e' are connected to the central reference terminal while start points 'A1s' and 'A2s' are connected to a feed line. Similarly, for phase B, coils 412-413 represented by resistances RB1 and RB2, respectively, are connected such that the end points 'B1e' and 'B2e' are connected to the central reference terminal while start points 'B1s' and 'B2s' are connected to a feed line, and for phase C, coils 414-415 represented by resistances RC1 and RC2, respectively, are connected such that the end points 'C1e' and 'C2e' are connected to the central reference terminal while start points 'C1s' and 'C2s' are connected to a feed line.

As with the configuration 650 in FIG. 6B, in the star configuration 660 as depicted in FIG. 6C, the direction of current flowing through coil A1 of stator 400 is the same as the direction of current flowing through coil A2. Similarly, the direction of current flowing through coil B1 of stator 400 is the same as the direction of current flowing through coil B2, and the direction of current flowing through coil C1 of stator 400 is the same as the direction of current flowing through coil C2. This means that coils A1 and A2 having the same direction of current flowing therethrough both interact with the same pole of the rotor. Additionally, coils B1 and B2 having the same direction of current flowing therethrough both interact with the same pole of the rotor. Further, coils C1 and C2 having the same direction of current flowing therethrough both interact with the same pole of the rotor. In effect, the coils of each phase in the double-winding stator 400 of the present disclosure see the same polarity of the magnet per pole pair of the rotor.

Figure 7:
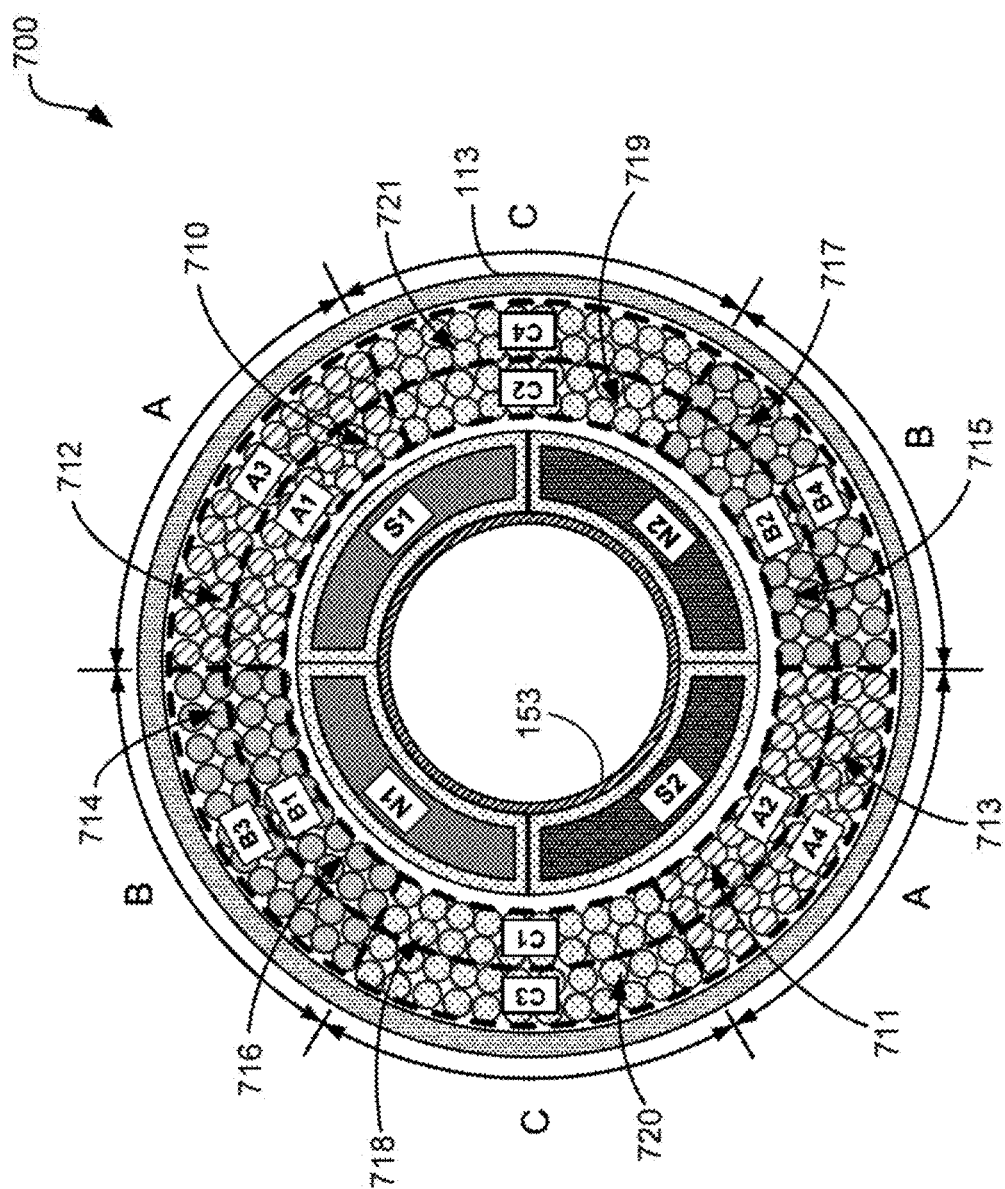
FIG. 7 shows an illustrative cross section of the blood pump of FIG. 1 using a double-winding stator for an electric motor having three phases and two pole pairs, according to an embodiment of the present disclosure.

FIG. 7 illustrates another example of a cross-section of a double-winding stator 700 for use in an electric motor having three phases A, B and C, and two permanent magnet pole pairs N1-S1 and N2-S2, according to an embodiment of the present disclosure. According the aforementioned general definitions, the electric motor using stator 700 has n=3 and p=2. As discussed in relation to stator 400 in FIG. 4, stator 700 also comprises two coils per phase per magnet pole pair resulting in 12 coils 710-721 in total. In the stator 700, due to the presence of two magnet pole pairs in the electric motor, each phase A, B and C of the three-phase electric motor comprises two coils. Thus, phase A comprises coils 710-73 (labelled 'A1,' 'A2,' 'A3' and 'A4' respectively), phase B comprises coils 714-717 (labelled 'B1,' 'B2,' 'B3' and 'B4' respectively), and phase C comprises coils 718-721 (labelled 'C1,' 'C2,' 'C3' and 'C4' respectively). As shown in FIG. 7, stator 700 comprises an inner winding of coils and an outer winding of coils. The inner winding comprises six coils in which one coil from each phase is arranged next to a coil from a different phase in a sequential order of phase per pole pair, the arrangement repeated about the circumference of the stator for all pole pairs such that each coil of the inner winding spans 360°/(np) =360°/(3)(2)=60° about the cross section of the stator 700, the inner winding having an exterior surface. The outer winding also comprises six coils arranged on the exterior surface of the inner winding, the coils from each phase in the outer winding circumferentially aligned with the coils from the inner winding having the same phase per pole pair such that each coil of the outer winding also spans 60° about the cross section of the stator 700. Further the coils of the same phase per pole pair may be connected in series or in parallel such that the current flowing through the coils is in the same direction.

As with the coils of stator 400, coils 710-721 may be electrically connected in either star or delta configuration in which (i) coils 710-713 for phase A are connected in series or in parallel with the start terminal of one coil connected to the end terminal of the next coil along the branch for phase A of the star or delta connection, (ii) coils 714-717 for phase B are connected in series or in parallel with the start terminal of one coil connected to the end terminal of the next coil along the branch for phase B of the star or delta connection, and (iii) coils 718-721 for phase C are connected in series or in parallel with the start terminal of one coil connected to the end terminal of the next coil along the branch for phase C of the star or delta connection. With such an electrical connection, (i) the direction of current flowing through coils A1 and A3 is the same as the direction of current flowing through coils A2 and A4, (ii) the direction of current flowing through coils B1 and B3 is the same as the direction of current flowing through coils B2 and B4, and (iii) the direction of current flowing through coils C1 and C3 is the same as the direction of current flowing through coils C2 and C4. In short, the current flowing through the coils of the same phase flows in the same direction, whether the coils of the same phase are connected in series or in parallel.

In this arrangement, coils A1-A4 have the same direction of current flowing therethrough, where coils A1 and A3 interact with pole S1, for example, and coils A2 and A4 interact with corresponding pole S2 of the same polarity as pole S1, for example, to cause rotation of the rotor. Similarly, coils B1-B4 have the same direction of current flowing therethrough, where coils B1 and B3 interact with pole N1, for example, and coils A2 and A4 interact with corresponding pole N2 of the same polarity as pole N1, for example, to cause rotation of the rotor. Further, coils C1-C4 have the same direction of current flowing therethrough, where coils C1 and C3 interact with pole S2, for example, and coils C2 and C4 interact with corresponding pole S1 of the same polarity to pole S2, for example, to cause rotation of the rotor. It should be noted that coils 710-721 may be driven by a six-step direct current controller, for example, which provides current to the coils 710-721 alternately in pairs of two phases at any one time. Thus, the coils from each phase generate torque in the rotor in turn, thereby causing continuous rotation of the rotor.

Figure 8:
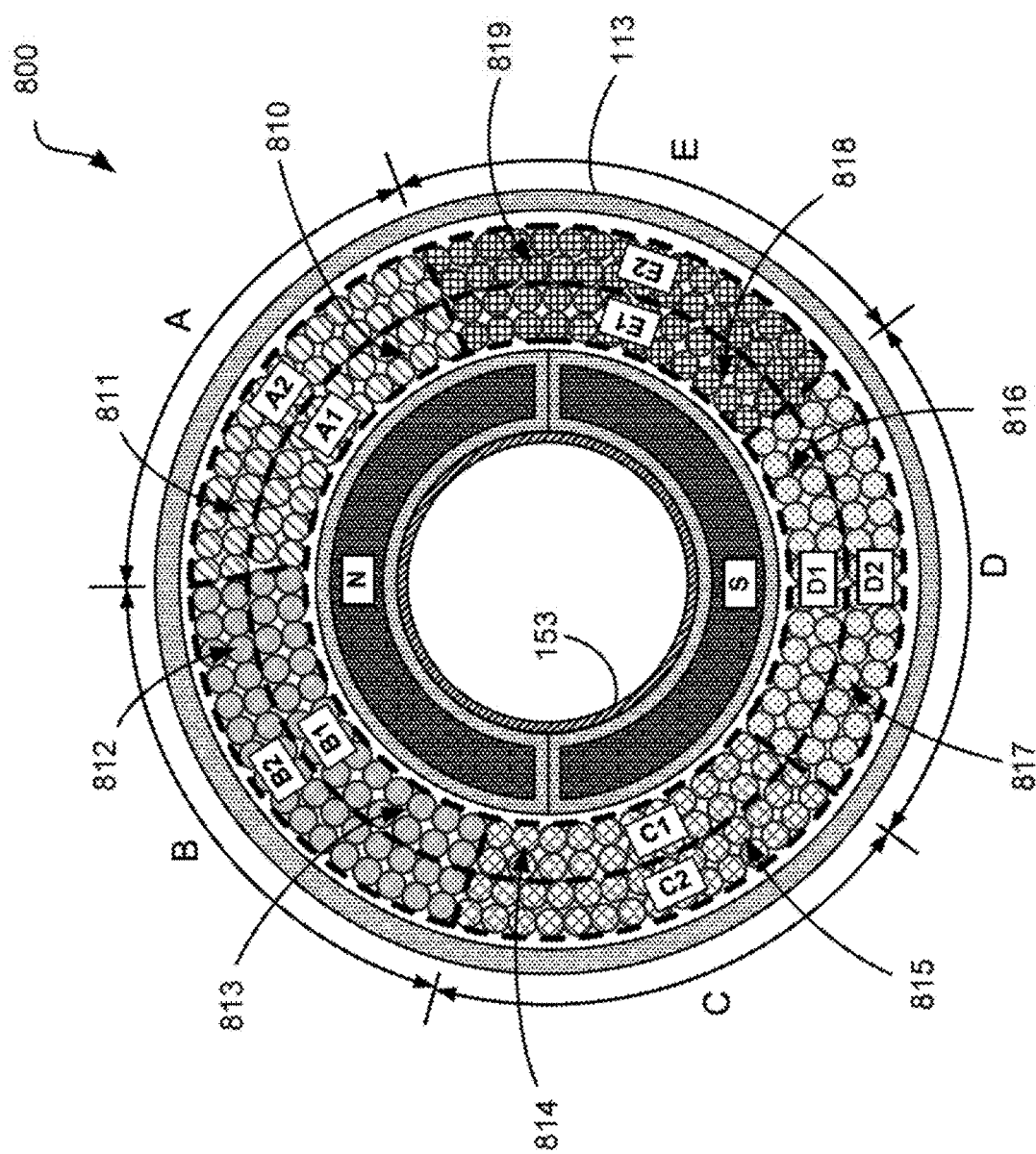
FIG. 8 shows an illustrative cross section of the blood pump of FIG. 1 using a double-winding stator for an electric motor having five phases and one pole pair, according to an embodiment of the present disclosure.

FIG. 8 illustrates a further example of a cross-section of a double-winding stator 800 for use in an electric motor having five phases A, B, C, D and E, and one permanent magnet pole pair N-S, according to an embodiment of the present disclosure. According the aforementioned general definitions, the electric motor using stator 800 has n=5 and p=1. As discussed in relation to stators 400 and 700, stator 800 also comprises two coils per phase per magnet pole pair resulting in 10 coils 810-819 in total. Phase A comprises coils 810-811 (labelled 'A1' and 'A2' respectively), phase B comprises coils 812-813 (labelled 'B1' and 'B2' respectively), phase C comprises coils 814-815 (labelled 'C1' and 'C2' respectively), phase D comprises coils 816-817 (labelled 'D1' and 'D2' respectively), and phase E comprises coils 818-819 (labelled 'E1' and 'E2' respectively). As shown in FIG. 8, stator 800 comprises and inner winding of coils and an outer winding of coils. The inner winding comprises five coils in which one coil from each phase is arranged next to a coil from a different phase in a sequential order of phase per pole pair, the arrangement repeated about the circumference of the stator for all pole pairs such that each coil of the inner winding spans 360°/(np) =360°/(5)(1) =72° about the cross section of the stator 800, the inner winding having an exterior surface. The outer winding also comprises five coils arranged on the exterior surface of the inner winding, the coils from each phase in the outer winding circumferentially aligned with the coils from the inner winding having the same phase per pole pair such that each coil of the outer winding also spans 72° about the cross section of the stator 800. Further the coils of the same phase per pole pair are connected in series or in parallel such that the current flowing through the coils is in the same direction.

As with the coils of stators 400 and 700, coils 810-819 may be electrically connected in either star or delta configuration in which (i) coils 810-811 for phase A are connected in series or in parallel with the start terminal of one coil connected to the end terminal of the next coil along the branch for phase A of the star or delta connection, (ii) coils 812-813 for phase are connected in series or in parallel with the start terminal of one coil connected to the end terminal of the next coil along the branch for phase B of the star or delta connection, (iii) coils 814-815 for phase C are connected in series or in parallel with the start terminal of one coil connected to the end terminal of the next coil along the branch for phase C of the star or delta connection, (iv) coils 816-817 for phase D are connected in series or in parallel with the start terminal of one coil connected to the end terminal of the next coil along the branch for phase D of the star or delta connection, and (v) coils 818-819 for phase E are connected in series or in parallel with the start terminal of one coil connected to the end terminal of the next coil along the branch for phase E of the star or delta connection. With such an electrical connection, (i) the direction of current flowing through coil A1 is the same as the direction of current flowing through coil A2, (ii) the direction of current flowing through coil B1 is the same as the direction of current flowing through coil B2, (iii) the direction of current flowing through coil C1 is the same as the direction of current flowing through coil C2, (iv) the direction of current flowing through coil DI is the same as the direction of current flowing through coil D2, and (v) the direction of current flowing through coil E1 is the same as the direction of current flowing through coil E2.

In this arrangement, coils A1-A2 have the same direction of current flowing therethrough, where coils A1-A2 interact with pole N, for example, at an instant in time. Similarly, coils for each of the other phases B-E interact with the same polarity of the magnetic flux from the rotor at any instant of time, the coils for each phase having the same direction of current flowing therethrough at said instant. Coils 810-819 are driven by a motor controller which provides current to the coils of multiple phases at any one time. Thus, the coils from each phase generate torque in the rotor in turn, thereby causing continuous rotation of the rotor.

Table 1 shows representative data for two blood pumps having electric motors with single helical winding and double helical winding stators, respectively. Specifically, the single helical winding stator is similar to the single-winding stator 300 as described in the foregoing, implemented with the helical winding type as shown in FIG. 2C. The double helical winding stator is similar to the double-winding stator 400 as described in the foregoing, also implemented with the helical winding type as shown in FIG. 2C. As can be seen, the double helical winding stator results in an electric motor with an increased coil resistance of 5.40 Ω/phase compared to that of the single helical winding stator, and with an increased torque constant of $1.236 \times 10^{-3}$ N·m/A, i.e. an increase of 40.5% from that of the single helical stator. The results in Table 1 confirm that the double-winding stator according to embodiments of the present disclosure reduces the coil joule heat by 40% while motors employing such a double-winding stator produce the same torque to drive the pumps compared to motors using a single-winding stator. It should be noted that blood pumps employing the above described stators comprising two coils per phase per magnet pole pair are configured to operate at a flow rate of about 1.0 lpm and about 6.0 lpm, where 'lpm' indicates liters per minute.

TABLE 1

Performance of blood pumps with various stator coil configurations.

| Stator coil type | 2-layer Helical Configuration | 4-layer Helical Configuration |
|---|---|---|
| Torque constant (N · m/A) × $10^{-3}$ | 0.88 | 1.236 |
| Coil Resistance per phase (Ω) | 4.60 | 5.40 |
| Average Current (mA) | 898 | 639 |
| Coil Heat (W) | 7.42 | 4.41 |

As described in the foregoing, increasing the number of magnet wires from a single-winding stator to a double-winding stator reduces the coil joule heat for the same output torque thus improves the overall efficiency of the motor. However, conventional implementation of increasing the number of winding turns will be described with respect to FIG. 9A. FIG. 9A shows an exemplary stator 900 having multiple layers of magnet wires in which the amount of conductor in the stator 900 is increased from the a two-layer stator. Stator 900 is suitable for use in a three-phase electric motor having phases A, B and C. As in the stators described in the foregoing, phase A comprises a coil 'A,' phase B comprises a coil 'B,' and phase C comprises a coil 'C'. As can be seen, the amount of conductor in each coil of the stator is increased by simply increasing the number of turns of magnet wire in each coil in a random manner. Here the wires are wound without any precision or regularity. For example, as shown in FIG. 9A, each of coils A, B and C is formed by the random placement of turns of magnet wires according to the numbers as shown starting at turn 1 and ending at turn 65. Within each coil the turns are placed randomly without any order as the objective is to pack the specific number of magnet wires within each coil. For example, turns 1-4 are spaced apart from each other as they are arranged to form the respective coil. This leads to a random collection of magnet wires in each coil which is an inferior use of space as the random placement gives rise to large gaps 910 forming as the coils are formed, for example, which may then be occupied by turns that are wound later in the winding sequence. This inefficient use of space within the respective coils results in a thick and oversized stator 900.

Figure 9B:
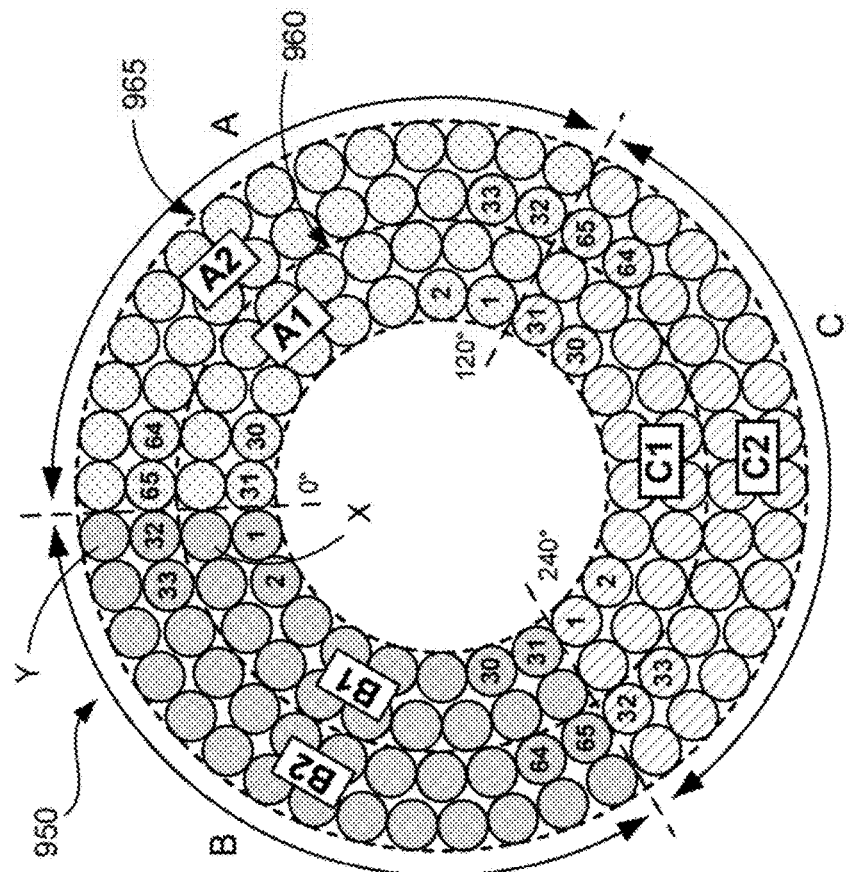
FIG. 9B shows the illustrative double-winding stator of FIG. 4, with a wire winding sequence used in the formation thereof, according to an embodiment of the present disclosure.
Figure 9A:
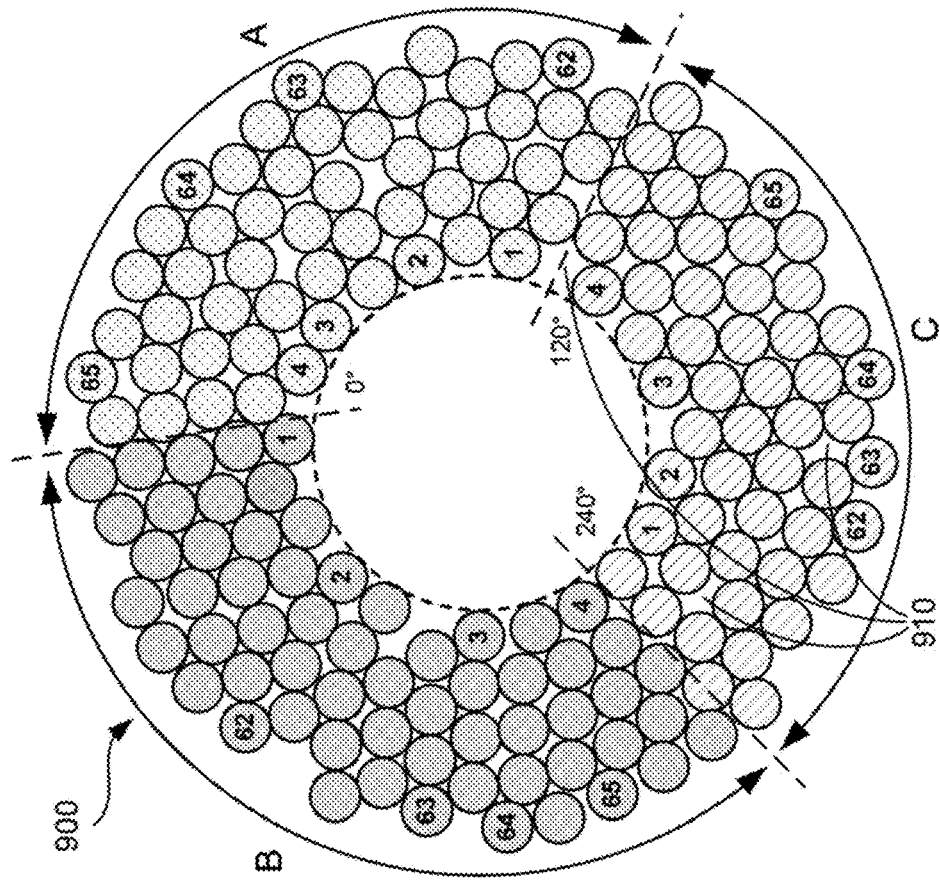
FIG. 9A shows an illustrative randomly wound multiple-layer stator with a wire winding sequence used in the formation thereof.
Figure 10A:
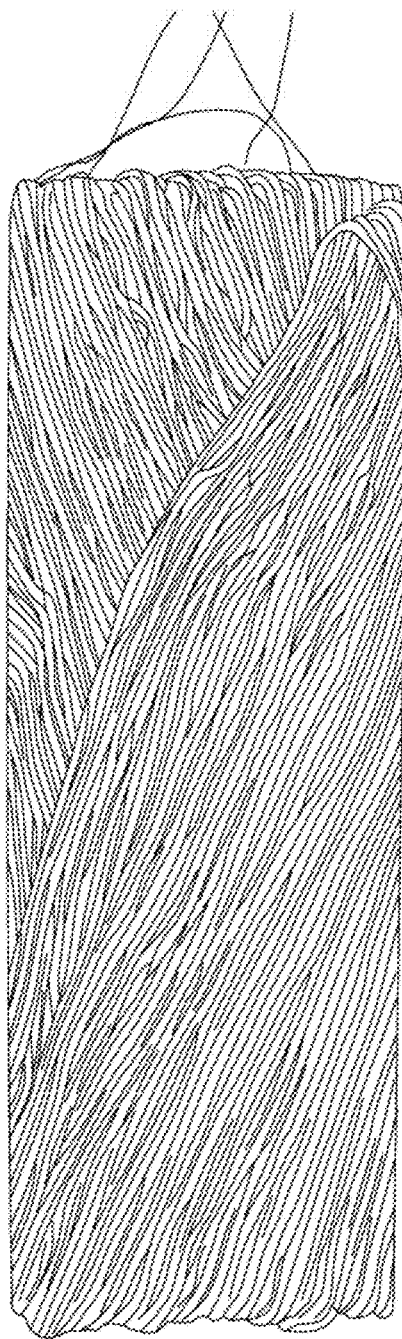
FIG. 10A shows an image of the randomly wound multiple-layer stator formed using the wire winding sequence of FIG. 9A.

FIG. 10A illustrates an exemplary randomly wound multiple-layer stator 900 formed using the winding sequence as described in relation to FIG. 9A. The random arrangement of wires forming the stator 900 can be seen in FIG. 10A where the magnet wires are irregular and excessively overlapped. This contributes to the irregular winding pattern of the exterior surface of the stator, as seen from the nature of the outer surface of the stator shown in FIG. 10A.

The oversized randomly wound multiple-layer stator 900 gives rise to several issues. Firstly, the stator will have to be mechanically squeezed to meet the size constrains of the motor stator. The mechanical squeezing may reduce the thickness of the stator 900 so that it will fit into the yoke of a motor which has a fixed inner diameter. Such mechanical squeezing is an additional post processing step that will be required after formation of the multiple-layer stator 900. Secondly, mechanical squeezing risks the integrity of the electrical insulation of magnet wires within each coil of the stator 900. This is because the force applied to mechanically squeeze the multiple-layer stator may cause the insulation around each magnet wire to be damaged. Such damaged insulation of the magnet wires may result in short circuits within and/or between coils during operation. It will be appreciated that without squeezing the randomly wound multiple-layer stator 900, the size of the magnets and/or the thickness of the yoke will have to be reduced thereby reducing the magnetic flux density B through the electric motor.

FIG. 9B illustrates an exemplary stator 950 having four layers of magnet wires formed into coils that are uniformly wound, according to an embodiment of the present disclosure. The four-layer coil stator 950 is similar to the double-winding stator 400 in FIGS. 4 and 5. As mentioned in the foregoing description, the stator of the present disclosure comprises an inner winding 960 and an outer winding 965. Each of the inner and outer windings comprise coils as shown in FIGS. 4 and 5. Further, each of the inner and outer windings comprises two layers of magnet wires formed into coils. Here, each coil A1, A2, B1, B2, C1 and C2 as shown in FIG. 9B is formed by winding magnet wires in an ordered sequence along the 120° span of the respective coil about the cross section of the stator between the proximal end of the stator, the magnet wires extending longitudinally towards the distal end, and returning back to the proximal end using any of the coil winding patterns shown in FIGS. 2E-2H.

When a magnet wire is wound to form a first turn (e.g. turn labelled '1') in each of the coils of the inner winding from the proximal end to the distal end of the stator, a forward portion of the magnet wire of turn 1 is formed in a first layer, and when the magnet wire is wound returning from the distal end to the proximal end, a return portion of the magnet wire (labelled 'X') of the turn 1 is formed in a second layer radially outwardly adjacent the first layer. Here, adjacent means "immediately radially next to" (i.e., without anything in between). Thus, the first turn is formed by a continuous copper wire wound from the proximal end of the stator to the distal end of the stator (forward wire portion arranged in the first layer), and from the distal end of the stator to the proximal end of the stator (return wire portion labelled 'X' arranged in the second layer). This is shown in the cross section of FIG. 9B where forward wire portion of turn 1 has a corresponding return wire portion X arranged immediately radially outward from forward wire portion. This forms coils having a first layer and a second layer within each of the inner winding 960 and outer winding 965 of stator 950, as shown in the cross section of FIG. 9B. This arrangement of magnet wires can be seen in the cross section of stator 950 in FIG. 9B where the turns in inner winding 960 are precisely laid in the sequential order from turn 1 to turn 31 in an anticlockwise direction along the span of the respective coil from 0° to 120° for each of the coils A1, B1 and C1. As the forward wire portion of each turn is laid in the first layer, the corresponding return wire portion is automatically laid in the second layer immediately radially outward from forward wire portion. Thus, for each turn, the forward wire portion (in the first layer) and the corresponding return wire portion (in the second layer) are formed before the subsequent turns of the remainder of the coil are formed. Each turn in each coil is formed immediately adjacent the previously formed turn, i.e. each turn is formed immediately next to the previous turn without anything in between.

The precise arrangement of turns in stator 950 results in the inner winding 960 forming a uniform exterior surface on which the wires of the outer winding 965 are arranged. Thus, after all the coils A1, B1 and C1 of the inner winding are formed, the coils A2, B2 and C2 of the outer winding are formed on the uniform exterior surface of the inner winding in a similar manner to which the inner winding is formed. For each of the coils of the outer winding, a first turn (e.g. turn labelled '32') is formed from the proximal end to the distal end of the stator where a forward portion of a magnet wire of the first turn 32 is formed in a third layer, and when the magnet wire is wound returning from the distal end to the proximal end, the return portion of the magnet wire (labelled 'Y') of the first turn 32 is formed in a fourth layer radially outwardly adjacent to the third layer. Thus the first turn 32 of the outer winding is formed by a continuous magnet wire wound from the proximal end of the stator to the distal end of the stator (forward wire portion arranged in the third layer), and from the distal end of the stator to the proximal end of the stator (return wire portion labelled 'Y' arranged in the fourth layer).

This arrangement of magnet wires can be seen in the cross section of stator 950 in FIG. 9B where the turns in outer winding 965 are precisely laid in the sequential order of turn 32 to turn 65 in an anticlockwise direction along the 120° span of the respective coils for each of the coils A2, B2 and C2. In this manner, turn 32 of the outer winding is radially aligned with turn 1 of the inner winding, and turn 65 of the wire winding is radially aligned with turn 31 of the inner winding. It should be noted that due to the larger diameter of the outer winding compared to the inner winding, the stator of the present disclosure has an outer winding with a larger number of turns than the inner winding. For example, in FIG. 9B, the double-winding stator 950, the outer winding has 34 turns and the inner winding has 31 turns. This results in a stator 950 comprising magnet wires that are ordered in a closely packed arrangement compared to the irregular arrangement of magnet wires in the randomly wound multiple-layer winding stator 900. The double-winding stator 950 is more compact and therefore has a smaller thickness compared to the randomly wound multiple-layer stator 900.

An exemplary winding sequence for the formation of stator 950 may have the following order: (1) form turns 1-31 for coil A1, (2) form turns 1-31 for coil B1, (3) form turns 1-31 for coil C1, (4) form turns 32-65 for coil A2 on the exterior surface of coil A1, (5) form turns 32-65 for coil B2 on the exterior surface of coil B1, and (6) form turns 32-65 for coil C2 on the exterior surface of coil C1. As previously described, each turn comprises a forward wire portion and a return wire portion automatically arranged radially adjacent the forward wire portion.

A servo motor is used to ensure the precise sequential placement of turns along the span of the respective stators. It should be noted that each coil in the inner winding and outer winding of the stator 950 has a pair of lead wires (such as lead wires 420-421 for coil A1 in FIG. 4) for connection to feed lines 146-147 of the electric motor 100.

In some implementations, in order to minimize the increase in coil resistance of the double-winding stator compared to the single-winding stator, thicker wires may be used for the coils forming the inner and outer windings to achieve a comparable resistance as the single-winding stator.

Figure 10B:
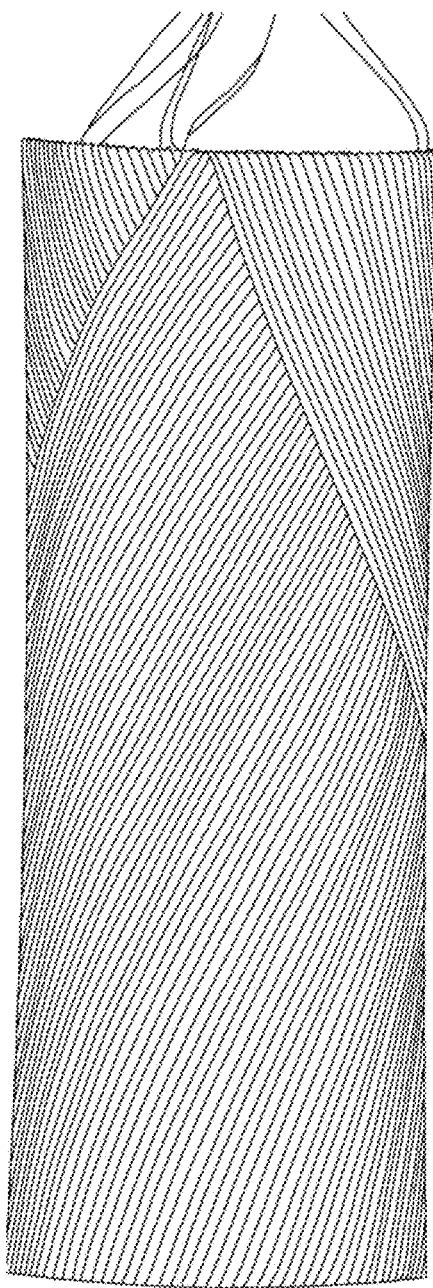
FIG. 10B shows an image of the double-winding stator formed using the wire winding sequence of FIG. 9B, according to an embodiment of the present disclosure.

FIG. 10B illustrates an exemplary stator formed using the winding sequence as described in relation to FIG. 9B according to embodiments of the present disclosure. As can be seen the stator in FIG. 10B comprises wires that are precisely arranged resulting in a uniform outer diameter along the length of the stator. Minimal mechanical squeezing of the stator would be required when assembling an electric motor with the four-layer coil stator of FIG. 9B. As minimal mechanical squeezing is needed, the risk of damage to the insulation of the wires forming coils A1, A2, B1, B2, C1 and C2 is minimized, thereby increasing the reliability of the double-winding stator 950.

It should also be noted that in respect of the randomly wound multiple-layer stator 900 in FIG. 9A, mechanical squeezing can only reduce the thickness of the stator to a limited extent. Thus, after mechanical squeezing, the randomly wound multiple-layer stator 900 may still be too thick for the yokes used in electrical motors compared to the double-winding stator 950. In order to alleviate this issue, in some embodiments, a thinner yoke is used with the randomly wound multiple-layer stator 900 compared to the double-winding stator 950 so as to preserve the outer diameter of the motor for integration with other components with which the motor operates, such as, for example the 14 Fr catheter through which the Impella® moves. Additionally, a rotor with smaller magnets may have to be used with the randomly wound multiple-layer stator 900 compared to the double-winding stator 950.

The thinner yoke and/or the smaller magnets reduces the magnetic flux density B within the electric motor having a randomly wound multiple-layer stator 900 compared to an electric motor having a double-winding stator 950. As shown in FIGS. 9A and 9B, both the randomly wound multiple-layer stator 900 and the double-winding stator 950 have the same number of winding turns. This means that both the stators 900, 950 have the same L contribution to the motor torque T, per equation (1). Using the same length of current-carrying wire L but lower flux density B leads to lower motor torque and lower motor efficiency in an electric motor having a randomly wound multiple-layer stator 900 compared to an electric motor having a double-winding stator 950.

Figure 11:
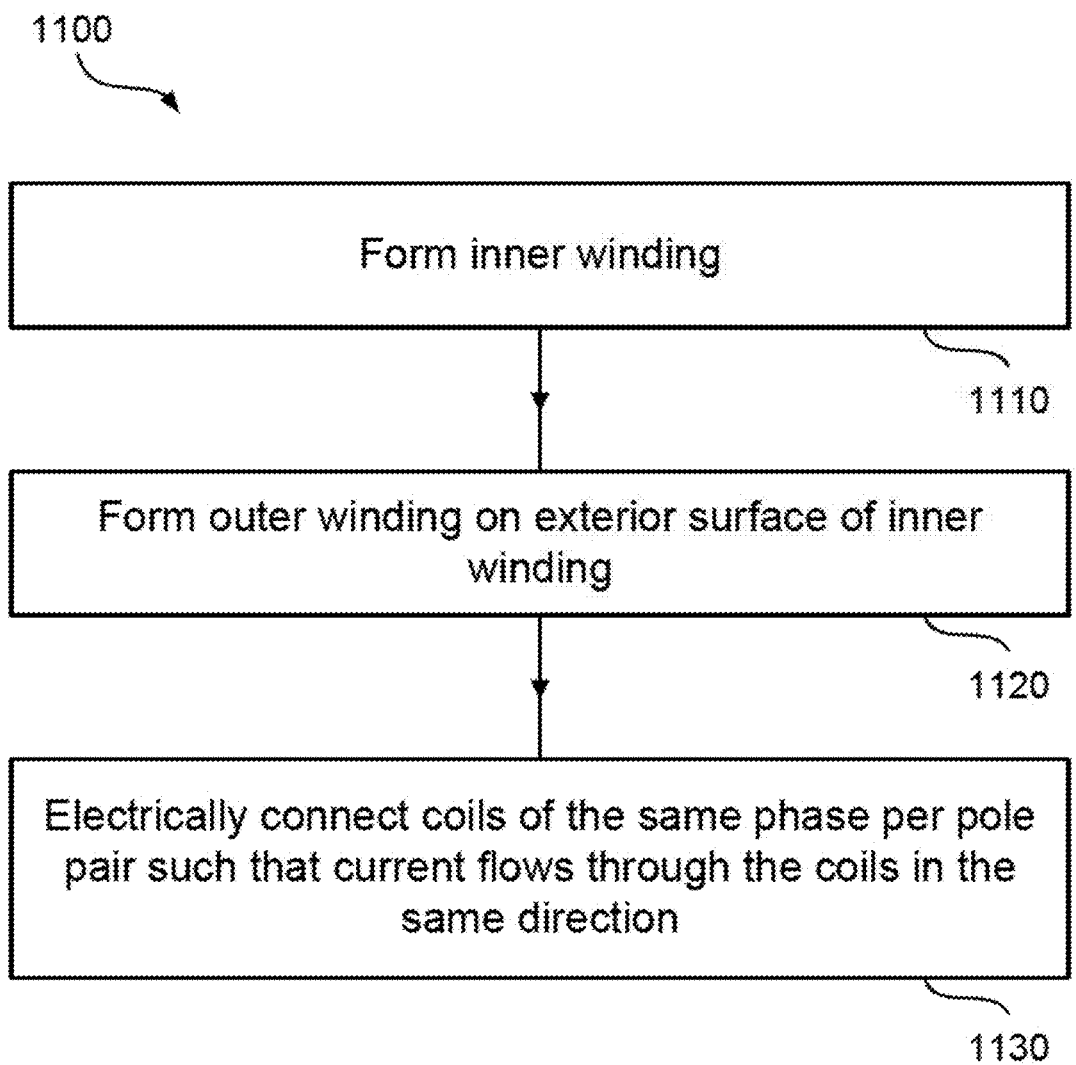
FIG. 11 shows illustrative flowchart of a method of forming the double-winding stators of FIGS. 4 and 9B, according to an embodiment of the present disclosure.

FIG. 11 illustrates an exemplary method 1100 of forming a double-winding stator, such as stator 400 as described in the foregoing description, according to an embodiment of the present disclosure. Method 1100 is suitable for the formation of a double-winding stator for use in a slotless permanent magnet motor having p magnet pole pairs and n phases, where p is an integer greater than zero, and n is an integer ≥3. The method 1100 begins at step 1110 in which an inner winding comprising np coils (such as inner winding 960 in FIG. 9B, for example) is formed. In the inner winding, one coil from each phase is arranged next to a coil from a different phase in a sequential order of phase per magnet pole pair, the arrangement repeated about the circumference of the stator for all pole pairs such that each coil of the inner winding spans 360/(np) mechanical degrees about the cross section of the double-winding stator. In some implementations, each winding comprises two layers of wires, each extending longitudinally along the length of the stator, wherein the wires in each winding are arranged immediately next to each other in a sequential order along the span of each winding. Once completed, the inner winding has an exterior surface.

After completing the inner winding, the method progresses to step 1120 in which the outer winding is wound, such as outer winding 965 in FIG. 9B, for example. Like the inner winding, the outer winding also comprises np coils, arranged on the exterior surface of the inner winding, the coils from each phase in the outer winding circumferentially aligned with the coils from the inner winding having the same phase per pole pair such that each coil of the outer winding also spans 360/(np) mechanical degrees about the cross section of the double-winding stator. As with the inner winding, in some implementations, each winding comprises two layers of wires, each extending longitudinally along the length of the stator, wherein the wires in each winding are arranged immediately next to each other in a sequential order along the span of each coil. With the arrangement as described in the foregoing, the inner and outer windings of the double-winding stator 950 share the same angular boundary.

Once the inner and outer windings are completed, the coils of the same phase per pole pair are electrically connected such that current flows through the coils of the same phase in the same direction, step 1130.

In summary, the double-winding stator of the present disclosure (e.g. stator 400) improves the efficiency of the motor when compared to the single-winding stator (e.g. stator 300) due to the tradeoff between the size of the rotor magnet, the yoke thickness and the number of winding turns in the respective stators. This increase in efficiency in the motor is achieved by an increase in the motor torque constant in the range of about 20% to about 50% while achieving a comparable stator resistance. In certain implementations of the present disclosure, the motor torque constant may be increased by about 25%, about 30%, about 35%, about 40% or about 45%. Additionally, the double-winding stator of the present disclosure (e.g. stator 950) improves the reliability of the motor compared to a randomly wound multiple-layer stator (e.g. stator 900) as minimal mechanical squeezing post processing is required due to the compact arrangement of wires in the double-winding stator. As minimal mechanical squeezing is necessary, no resulting wire insulation damage is present in the double-winding stator, unlike the randomly wound multiple-layer stator where excessive mechanical squeezing is required.

From the foregoing and with reference to the various figure drawings, those skilled in the art will appreciate that certain modifications can also be made to the present disclosure without departing from the scope of the same. It is to be understood that the devices described herein, while shown with respect to a double-winding stator of an electric motor for a blood pump, may be applied to other systems in which the electric motor with increased torque and high motor efficiency is desired. While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

In the foregoing disclosure, it will be understood that the term 'about' should be taken to mean ±20% of the stated value. Additionally, the term 'electric motor' should be taken to be synonymous with the term electric machine, as is widely known in the art. Further, the term 'adjacent' should be taken to mean immediately next to without anything intermediate in between. For example, object/feature P is adjacent object/feature Q when there are no intermediate object(s) between P and Q. All measure of degrees (with unit °) should be taken as mechanical degrees unless otherwise stated. In the foregoing embodiments, the wires used for the windings of the stator may comprise any material, such as, for example, copper. In some implementations, the wires may be insulated.

Variations and modifications will occur to those of skill in the art after reviewing this disclosure. The disclosed features may be implemented, in any combination and subcombination (including multiple dependent combinations and subcombinations), with one or more other features described herein. The various features described or illustrated above, including any components thereof, may be combined or integrated in other systems. Moreover, certain features may be omitted or not implemented.

Examples of changes, substitutions, and alterations are ascertainable by one skilled in the art and could be made without departing from the scope of the information disclosed herein. All references cited herein are incorporated by reference in their entirety and made part of this application.

The invention claimed is:

1. An intravascular blood pump for insertion into a patient's heart, the intravascular blood pump comprising:
   a motor comprising a stator that magnetically interacts with a rotor for rotation thereof; and
   an elongate housing having a proximal end and a distal end, the housing having a longitudinal axis; and
   wherein the motor is a slotless permanent magnet motor contained within the housing and supported for rotation upon magnetic interaction with the stator, thereby causing the rotor to rotate, the motor having p magnet pole pairs and n phases, where p is an integer ≥ to 1, and n is an integer ≥ 3,
   wherein the stator extends along the longitudinal axis of the housing and has 2np coils wound to form two coils per phase per magnet pole pair, the stator comprising:
      an inner winding comprising np coils in which one coil from each phase is arranged next to a coil from a different phase in a sequential order of phase per pole pair, the inner winding having an exterior surface, and
      an outer winding also comprising np coils arranged on the exterior surface of the inner winding, the coils from each phase in the outer winding circumferentially aligned with the coils from the inner winding having the same phase per pole pair;
   wherein the coils of the same phase per pole pair are electrically connected such that a current flowing through the coils is in the same direction.

2. The intravascular blood pump of claim 1, wherein each coil of the inner winding and each coil of the outer winding comprises two layers of magnet wires, each extending longitudinally along a length of the stator.

3. The intravascular blood pump of claim 2, wherein the magnet wires in each coil are arranged next to each other in a sequential order along a span of the coil.

4. The intravascular blood pump of claim 1, wherein the inner winding of coils establishes a uniform surface upon which the outer winding of coils is overlaid.

5. The intravascular blood pump of claim 1, wherein the coils of a phase are electrically connected to the coils of the other phases in either a star or a delta configuration.

6. The intravascular blood pump claim 5, wherein the coils of the same phase are connected either in series or in parallel.

7. The intravascular blood pump of claim 1, wherein each coil of the 2np coils has a coil winding pattern selected from the group consisting of helical winding patterns, rhombic winding patterns, and hybrid winding patterns.

8. The intravascular blood pump of claim 1, wherein the motor comprises a three-phase one pole pair machine.

9. The intravascular blood pump of claim 8, wherein the motor comprises a six-coil two-pole machine, each coil spanning 120 mechanical degrees about a cross section of the stator.

10. The intravascular blood pump of claim 1, wherein the intravascular blood pump pumps blood at a rate between about 1 lpm and about 6 lpm.

11. A slotless permanent magnet electric motor having p magnet pole pairs and n phases, where p is an integer ≥ 1, and n is an integer ≥ 3, the electric motor having a longitudinal axis and comprising:
    a stator extending along the longitudinal axis and having 2np coils wound to form two coils per phase per magnet pole pair, the stator comprising:
       an inner winding comprising np coils in which one coil from each phase is arranged next to a coil from a different phase in a sequential order of phase per pole pair, the inner winding having an exterior surface, and
       an outer winding also comprising np coils arranged on the exterior surface of the inner winding, the coils from each phase in the outer winding circumferentially aligned with the coils from the inner winding having the same phase per pole pair,
    wherein the coils of the same phase per pole pair are electrically connected such that a current flowing through the coils is in the same direction,
    wherein the electric motor is configured to be used in an intravascular blood pump, the intravascular blood pump comprising the electric motor contained within a housing of the intravascular blood pump.

12. The electric motor of claim 11, wherein each coil of the inner winding and each coil of the outer winding comprises two layers of magnet wires, each extending longitudinally along a length of the stator.

13. The electric motor of claim 12, wherein the magnet wires in each coil are arranged next to each other in a sequential order along a span of the coil.

14. The electric motor of claim 11, wherein the inner winding of coils establishes a uniform foundation upon which the outer winding of coils is overlaid.

15. The electric motor of claim 11, wherein the coils of a phase are electrically connected to the coils of the other phases in either a star or a delta configuration.

16. The electric motor of claim 15, wherein the two coils per phase are connected either in series or in parallel.

17. The electric motor of claim 11, wherein each coil of the 2np coils has a coil winding pattern selected from the group consisting of helical winding patterns, rhombic winding patterns, and hybrid winding patterns.

18. The electric motor of claim 17, wherein the electric motor comprises a three-phase two-pole machine.

19. The electric motor of claim 18, wherein the electric motor comprises a six-coil two-pole machine, each coil spanning 120 mechanical degrees about a cross section of the stator.

20. The electric motor of claim 11, wherein the electric motor is disposed in a blood pump that pumps blood at a rate between about 1 lpm and about 6 lpm.

* * * * *